(12) United States Patent
Fujiwara et al.

(10) Patent No.: US 8,759,617 B2
(45) Date of Patent: Jun. 24, 2014

(54) METHOD FOR EXTRACTION AND PURIFICATION OF RECOMBINANT PROTEINS FROM TRANSGENIC PLANTS

(75) Inventors: Yoshihiro Fujiwara, Ibaraki (JP); Kenji Sekikawa, Ibaraki (JP); Yasuhiko Aiki, Ibaraki (JP); Fumio Takaiwa, Ibaraki (JP); Lijun Yang, Ibaraki (JP)

(73) Assignees: National Institute of Agrobiological Sciences, Ibaraki (JP); Preventec, Inc., Ibaraki (JP)

( * ) Notice: Subject to any disclaimer, the term of this patent is extended or adjusted under 35 U.S.C. 154(b) by 200 days.

(21) Appl. No.: 13/237,327

(22) Filed: Sep. 20, 2011

(65) Prior Publication Data
US 2012/0142033 A1 Jun. 7, 2012

Related U.S. Application Data

(60) Provisional application No. 61/385,077, filed on Sep. 21, 2010, provisional application No. 61/441,464, filed on Feb. 10, 2011.

(51) Int. Cl.
*A01H 5/00* (2006.01)
*C07H 21/04* (2006.01)
*C07K 14/00* (2006.01)

(52) U.S. Cl.
USPC .............................. 800/295; 536/23.1; 514/2

(58) Field of Classification Search
None
See application file for complete search history.

(56) References Cited

U.S. PATENT DOCUMENTS

2012/0328561 A1   12/2012   Fujiwara et al.

OTHER PUBLICATIONS

Viana et al., "Heterologous Production of Peptides in Plants: Fusion Proteins and Beyond", Current Protein and Peptide Science vol. 14, pp. 568-579 (2013).*

* cited by examiner

*Primary Examiner* — Anand Desai
(74) *Attorney, Agent, or Firm* — Cook Alex Ltd.

(57) ABSTRACT

Extraction and purification of recombinant proteins rendered difficult to extract from transgenic plants by using an extraction solution containing reducing agents and surfactants or an extraction solution containing reducing agents and organic solvents.

33 Claims, 14 Drawing Sheets

Figure 1

Gene sequence (SEQ ID NO:1) and amino acid sequence (SEQ ID NO:2) of rice-type hIL-10

```
         10         20         30         40         50         60
AGTCCAGGCCAAGGAACTCAGTCTGAAATAGCTGCACACTTCCCTGGCAATCTCCCA
 S  P  G  Q  G  T  Q  S  E  N  S  C  T  H  F  P  G  N  L  P 70         80         90        100        110        120
AACATGCTTCGTGATTTGAGGGATGCATTCAGTCGTGTTAAGACCTTCTTTCAAATGAAG
 N  M  L  R  D  L  R  D  A  F  S  R  V  K  T  F  F  Q  M  K 130        140        150        160        170        180
GATCAACTAGATAATCTCCTTCTAAAGGAGAGTTTGCTCGAAGATTTCAAGGGTTACTTG
 D  Q  L  D  N  L  L  K  E  S  L  L  E  D  F  K  G  Y  L 190        200        210        220        230        240
GGATGTCAGGCTCTTTCTGAGATGATCCAATTCTACCTAGAGAAGAGGTAATGCCACAGGCA
 G  C  Q  A  L  S  E  M  I  Q  F  Y  L  E  E  V  M  P  Q  A 250        260        270        280        290        300
GAAAACCAAGATCCTGATATTAAGGCACATGTTAATAGCCTCGGAGAGAACCTTAAGACT
 E  N  Q  D  P  D  I  K  A  H  V  N  S  L  G  E  N  L  K  T 310        320        330        340        350        360
CTAAGGTTGAGACTTCGTAGGTGCCACAGATTCCTACCCTGTGAAAATAAGAGTAAGGCT
 L  R  L  R  R  C  H  R  F  L  P  C  E  N  K  S  K  A 370        380        390        400        410        420
GTTGAACAAGTTAAGAACGCATTCAATAAGCTCCAGGAGAAGGGCATCTATAAGGCAATG
 V  E  Q  V  K  N  A  F  N  K  L  Q  E  K  G  I  Y  K  A  M 430        440        450        460        470        480
TCTGAGTTCGATATTTCATTAATTACATAGAGGCTTATATGACAATGAAGATTCGTAAC
 S  E  F  D  I  F  I  N  Y  I  E  A  Y  M  T  M  K  I  R  N 490        500        510        520
CACCACCATCACCATCATAAGGATGAGTTGTAA
 H  H  H  H  H  H  K  D  E  L  *
```

Figure 8

Summary of IL-10 Purification

|  | Total protein (mg) | IL-10 (mg) | Recovery Rate (%) | Purity (%) |
|---|---|---|---|---|
| Extraction (Rice Powder 40g) | 1040.81 | 48.2 | 100 | 4.6 |
| Ni Affinity | 71.31 | 46.4 | 96.3 | 65.2 |
| Ni affinity 2nd time | 31.60 | 23.7 | 49.2 | 75.0 |
| Refolding | 26.28 | 19.6 | 40.6 | 74.4 |
| Anion Exchange | 7.31 | 6.3 | 13.1 | 86.2 |
| Cation Exchange | 3.39 | 3.3 | 6.8 | 96.5 |
| Gel Filtration | 2.05 | 2.1 | 4.3 | 100 | though its biological activity varies widely, the foremost characteristic differentiating it from

SEQUENCE LISTING

```
<160> NUMBER OF SEQ ID NOS: 1

<210> SEQ ID NO 1
<211> LENGTH: 513
<212> TYPE: DNA
<213> ORGANISM: Homo sapiens
<220> FEATURE:
<221> NAME/KEY: CDS
<222> LOCATION: (1)..(510)
<223> OTHER INFORMATION: Codon was modified for expression in rice
<220> FEATURE:
<221> NAME/KEY: misc_feature
```

```
<222> LOCATION: (481)..(492)
<223> OTHER INFORMATION: 6xHis
<220> FEATURE:
<221> NAME/KEY: misc_feature
<222> LOCATION: (499)..(510)
<223> OTHER INFORMATION: ER retention sequence

<400> SEQUENCE: 1 agt cca ggc caa gga act cag tct gaa aat agc tgc aca cac ttc cct      48
Ser Pro Gly Gln Gly Thr Gln Ser Glu Asn Ser Cys Thr His Phe Pro
1               5                   10                  15 ggc aat ctc cca aac atg ctt cgt gat ttg agg gat gca ttc agt cgt      96
Gly Asn Leu Pro Asn Met Leu Arg Asp Leu Arg Asp Ala Phe Ser Arg
                20                  25                  30 gtt aag acc ttc ttt caa atg aag gat caa cta gat aat ctc ctt cta     144
Val Lys Thr Phe Phe Gln Met Lys Asp Gln Leu Asp Asn Leu Leu Leu
            35                  40                  45 aag gag agt ttg ctc gaa gat ttc aag ggt tac ttg gga tgt cag gct     192
Lys Glu Ser Leu Leu Glu Asp Phe Lys Gly Tyr Leu Gly Cys Gln Ala
50                  55                  60 ctt tct gag atg atc caa ttc tac cta gaa gag gta atg cca cag gca     240
Leu Ser Glu Met Ile Gln Phe Tyr Leu Glu Glu Val Met Pro Gln Ala
65                  70                  75                  80 gaa aac caa gat cct gat att aag gca cat gtt aat agc ctc gga gag     288
Glu Asn Gln Asp Pro Asp Ile Lys Ala His Val Asn Ser Leu Gly Glu
                85                  90                  95 aac ctt aag act cta agg ttg aga ctt cgt agg tgc cac aga ttc cta     336
Asn Leu Lys Thr Leu Arg Leu Arg Leu Arg Arg Cys His Arg Phe Leu
            100                 105                 110 ccc tgt gaa aat aag agt aag gct gtt gaa caa gtt aag aac gca ttc     384
Pro Cys Glu Asn Lys Ser Lys Ala Val Glu Gln Val Lys Asn Ala Phe
        115                 120                 125 aat aag ctc cag gag aag ggc atc tat aag gca atg tct gag ttc gat     432
Asn Lys Leu Gln Glu Lys Gly Ile Tyr Lys Ala Met Ser Glu Phe Asp
    130                 135                 140 att ttc att aat tac ata gag gct tat atg aca atg aag att cgt aac     480
Ile Phe Ile Asn Tyr Ile Glu Ala Tyr Met Thr Met Lys Ile Arg Asn
145                 150                 155                 160 cac cac cat cac cat cat aag gat gag ttg taa                          513
His His His His His His Lys Asp Glu Leu
                165                 170
```

METHOD FOR EXTRACTION AND PURIFICATION OF RECOMBINANT PROTEINS FROM TRANSGENIC PLANTS

RELATED APPLICATIONS

This application is a non-provisional application which claims the benefit of prior filed U.S. provisional application Ser. No. 61/385,077, filed Sep. 21, 2010 and U.S. provisional application Ser. No. 61/441,464, filed Feb. 10, 2011 both of which are incorporated by reference herein in their entirety.

FIELD OF THE INVENTION

The present invention relates to a method for the extraction and purification of recombinant proteins rendered difficult to extract from transgenic plants. Further, the present invention relates to a method for the extraction and purification of recombinant interleukin 10 (recombinant IL-10) from transgenic plants. Furthermore, the present invention relates to an endotoxin free recombinant human IL-10 (recombinant hIL-10).

BACKGROUND OF THE INVENTION

Recombinant proteins have been manufactured conventionally by the recombinant technologies using microbes such as *E. coli*, etc., cultured mammalian cells, or the like Windsor, et al., Biochemistry 32, 8807-15 (1993); Bondoc, et al., Anal. Biochem. 246, 234-8 (1997); Ball, et al., Eur. Cytokine Netw. 12, 187-93 (2001).). However, in cases where cultured mammalian cells are used as the host cells, it has become enormously costly to manufacture a large scale of recombinant proteins. Furthermore, in such cases using microbes and cultured mammalian cells there exists inevitably a serious risk of contamination of pathogens such as human-infectious viruses, prions, endotoxins etc (Schillberg, et al., Naturwissenschaften 90, 145-55 (2003).).

The gene expression of recombinant proteins in the rice seeds is reported (Takaiwa, et al., Plant Biotechnology 5, 84-92 (2007).). The rice seeds are known as sites for the accumulation of proteins and a small number of different storage proteins are accumulated in their special organelles called "protein granules". Vectors using a storage protein promoter are reported for the recombinant proteins in the rice seeds. (Yang, et al, Plant Biotechnology 5, 815-26 (2007).).

IL-10 is a cytokine produced mainly by varieties of lymphocytes such as type-2 helper T cells (Th2), regulatory T cells and the like. Although its biological activity varies widely, the foremost characteristic differentiating it from other cytokines is a suppressive activity. IL-10 suppressively controls immune function by inhibiting the production of inflammatory cytokines such as interferon-γ" (IFN-γ) and the like (Moore, et al., Annu. Rev. Immunol. 19, 683-765 (2001).). Thus, it is expected that IL-10 may be used as a drug for treatment of inflammatory diseases, allergic diseases, and autoimmune diseases (Asadullah, et al., Pharmacol. Rev. 55, 241-69 (2003).).

A biologically inactive form of IL-10 is a monomer with a molecular weight of 18.5 kDa, and its active form is a non-covalent homodimer with a molecular weight of 37 kDa (Syto, et al., Biochemistry 37, 16943-51 (1998).). The monomer has two sets of intra-molecular disulfide bonds, and the disulfide bonds are necessary to maintain the spatial protein structure. However, the monomer cannot exist stably only by itself. On the other hand, biologically active IL-10 consisting of two monomers connected each other by inter-molecular non-covalent bonds can exist stably only by itself. In other words, the disulfide bonds in the monomer and the non-covalent bonds connecting the sub-units of two monomers are necessary to maintain the spatial protein structure and the biological activity of IL-10, and IL-10, when these either bonds are destroyed, is irreversibly denatured and loses its biological activity. IL-10 is denatured and deactivated at high temperature or in acidic conditions (pH 6 or less). There are several reports on IL-10 refolding methods (Bondoc, et al., Anal. Biochem. 246, 234-8 (1997); Ball, et al., Eur. Cytokine Netw. 12, 187-93 (2001).) in order to obtain a biologically active form of IL-10 from its denatured monomers. However, highly efficient refolding methods of IL-10 have not been developed.

Furthermore, bioactivity assay methods are used for detecting a biologically active form of IL-10. However, such methods require a technical skill and a long time. The highly efficient and conventional methods for refolding IL-10 and detecting a biologically active form of IL-10 have not been developed.

There are cases that recombinant proteins can not be extracted from transgenic plants by commonly known extraction buffer solutions containing a buffer agent, for example tris(hydroxymethyl)aminomethane (Tris) and phosphoric acid, and a surfactant, for example a non-ionic surfactant. However, practical and highly efficient extraction methods for such recombinant proteins, without losing their native structures and biological activities, have not been developed.

SUMMARY OF THE INVENTION

It is an objective of the present invention to provide a method for the extraction and purification of recombinant proteins rendered difficult to extract from transgenic plants. It is another objective of the present invention to provide a method for the extraction and purification of biologically active recombinant IL-10. It is another objective of the present invention to provide a biologically active and safe recombinant IL-10.

The present inventors, as a result of insightful studies to solve the above problems in this field, have developed a novel and practically efficient method for extracting and purifying recombinant proteins rendered difficult to extract from transgenic plants, and specifically recombinant IL-10, by using a combination of reducing agents and surfactants, and by using another combination of organic solvent and reducing agents, specifically n-propanol and β-mercaptoethanol (bME) as a reducing agent. The present inventors have further developed a novel and practically efficient method for providing a biologically active recombinant IL-10 maintaining the spatial protein structure of natural IL-10. Furthermore, the present inventors have developed a novel and practically efficient method for providing a biologically active and safe recombinant hIL-10.

The present invention is summarized as follows:
(1) A method for extracting and purifying a recombinant protein rendered difficult to extract from a transgenic plant, comprising a step of extracting by using an extraction solution containing a reducing agent and a surfactant;
(2) The method according to (1), wherein extracting from a part of the transgenic plant selected from: an organ, a tissue, a seed, a callus, a cell and a shoot;
(3) The method according to (2), wherein extracting from a seed of the transgenic plant;

(4) The method according to any one of (1) to (3), wherein the recombinant protein rendered difficult to extract is expressed in the transgenic plant, and is in a state selected from a group comprising:
(a) an encapsulated state in an inclusion body;
(b) an encapsulated state in a protein body;
(c) a state of an aggregated form;
(d) a state where an intra-molecular disulfide bond is formed incorrectly in the recombinant protein;
(e) a state where an inter-molecular non-covalent bond is formed incorrectly between sub-units in the recombinant protein;
(f) a state bonded to a plant protein in the transgenic plant;
(g) a state that substantially only the plant protein other than the recombinant protein is extracted by using an extraction solution selected from a group comprising: an extraction solution containing urea, an extraction solution containing guanidine, an extraction solution containing n-propanol, an extraction solution containing n-propanol and β-mercaptoethanol, and an extraction solution containing NaCl, an extraction solution containing NaCl and n-propanol, and an extraction solution containing NaCl, n-propanol and β-mercaptoethanol;
(5) The method according to any one of (1) to (4), wherein the transgenic plant is a plant selected from a group comprising: tobacco, cabbage, lettuce, rice, potato, cucumber, eggplant, tomato, barley, wheat, maize, rye, sorghum, rapeseed, cotton, mustard, *Arabidopsis thaliana*, sunflower, alfalfa, chickpea, clover, pea, peanuts, yellow split pea, broad bean, *Medicago polymorphs*, cassava, water lentil, water hyacinth, citrus, peach and apple;
(6) The method according to anyone of (1) to (5), wherein the transgenic plant is a rice plant;
(7) The method according to any one of (1) to (6), including an additional pre-extraction step of extracting a plant protein prior to extracting the recombinant protein;
(8) The method according to (7), wherein extracting the plant protein by using an extraction solution selected from a group comprising; an extraction solution containing urea, an extraction solution containing guanidine, an extraction solution containing n-propanol, an extraction solution containing n-propanol and β-mercaptoethanol, and an extraction solution containing NaCl, an extraction solution containing NaCl and n-propanol, and an extraction solution containing NaCl, n-propanol and β-mercaptoethanol;
(9) The method according to (7) or (8), wherein the plant protein is selected from a group comprising: prolamin, cys-prolamin, globulin and glutelin;
(10) The method according to (9), wherein extracting glutelin by the steps selected from a group comprising:
(a) extracting by using an extraction solution containing NaCl and extracting by using an extraction solution containing acetone, NaCl and β-mercaptoethanol; and
(b) extracting by using an extraction solution containing NaCl and extracting by using an extraction solution containing lactic acid;
(11) The method according to any one of (1) to (10), wherein the reducing agent is a reducing agent having an ability of reducing a disulfide bond;
(12) The method according to any one of (1) to (11), wherein the reducing agent is selected from a group comprising: dithiothreitol, reduced glutathione, β-mercaptoethanol, tris(2-carboxyethyl) phosphine hydrochloride, cysteine, 2-mercaptoethylamine, ascorbic acid and 3-mercaptopropionic acid;
(13) The method according to any one of (1) to (12), wherein the reducing agent is selected from a group comprising: dithiothreitol and β-mercaptoethanol;
(14) The method according to any one of (1) to (13), wherein the surfactant is selected from a group comprising: 3-[(3-cholamidopropyl)dimethylammonio]-1-propane-sulfonate, sodium cholate, sodium deoxycholate, sodium lauryl sarcosine, sodium lauryl benzene sulfonate, Triton X-100, Triton X-114, Tween 20, Tween 40, Tween 60, Tween 80, C7BzO, SB3-10, SB3-14, Amidosulfobetaine-14, cetyl trimethylammonium bromide and sodium dodecyl sulfate;
(15) The method according to any one of (1) to (14), wherein the surfactant is selected from a group comprising: cetyl trimethylammonium bromide and sodium dodecyl sulfate;
(16) A method for extracting a recombinant protein rendered difficult to extract from a transgenic plant, comprising the steps of:
(a) extracting a plant protein by using an extraction solution selected from a group comprising: an extraction solution containing urea, an extraction solution containing guanidine, an extraction solution containing n-propanol, an extraction solution containing n-propanol and β-mercaptoethanol, an extraction solution containing NaCl, an extraction solution containing NaCl and n-propanol and an extraction solution containing NaCl, n-propanol and β-mercaptoethanol; and
(b) extracting the recombinant protein by using an extraction solution containing a water-soluble lower alkanol and a reducing agent having an ability of reducing a disulfide bond;
(17) The method according to (16), wherein:
(a) the recombinant protein rendered difficult to extract is a recombinant protein being expressed in the seeds of the transgenic plant and being in a state selected from a group comprising: an encapsulated state in an inclusion body, an encapsulated state in a protein body, an aggregated state, a state where an intra-molecular disulfide bond is formed incorrectly in the recombinant protein, a state where an inter-molecular non-covalent bond is formed incorrectly between sub-units in the recombinant protein, and a state bonded to a plant protein in the transgenic plant;
(b) the water-soluble lower alkanol is selected from a group comprising: n-propanol, propanol, n-butanol, s-butanol, t-butanol; and
(c) the reducing agent is selected from a group comprising: dithiothreitol, reduced glutathione, β-mercaptoethanol, tris(2-carboxyethyl) phosphine hydrochloride, cysteine, 2-mercaptoethylamine, ascorbic acid and 3-mercaptopropionic acid;
(18) The method according to (16) or (17), wherein extracting from a part of the transgenic plant selected from: an organ, a tissue, a seed, a callus, a cell and a shoot;
(19) The method according to any one of (16) to (18), wherein extracting from a seed of the transgenic plant;
(20) The method according to any one of (16) to (19), wherein the transgenic plant is a plant selected from a group comprising: tobacco, cabbage, lettuce, rice, potato, cucumber, eggplant, tomato, barley, wheat, maize, rye, sorghum, rapeseed, cotton, mustard, *Arabidopsis thaliana*, sunflower, alfalfa, chickpea, clover, pea, peanuts, yellow split pea, broad bean, *Medicago polymorpha*, cassava, water lentil, water hyacinth, citrus, peach and apple;
(21) The method according to any one of (16) to (20), wherein the transgenic plant is a rice plant;

(22) The method according to any one of (16) or (21), comprising the steps of:
extracting the plant protein by using an extraction solution containing NaCl and extracting the recombinant protein by using an extraction solution containing n-propanol and β-mercaptoethanol;
(23) The method according to any one of (16) to (22), wherein the plant protein is selected from a group comprising: prolamin, cys-prolamin, globulin and glutelin;
(24) The method according to any one of (16) to (23), wherein extracting glutelin by the steps selected from a group comprising:
(a) extracting by using an extraction solution containing NaCl and extracting by using an extraction solution containing acetone, NaCl and β-mercaptoethanol; and
(b) extracting by using an extraction solution containing NaCl and extracting by using an extraction solution containing lactic acid;
(25) The method according to any one of (1) to (24), including the additional steps for the extracted recombinant protein comprising:
(a) purifying the extracted recombinant protein by an affinity column chromatography;
(b) refolding the purified recombinant protein by using a refolding agent; and
(c) purifying the refolded recombinant protein by an anion exchange column chromatography;
(26) The method according to (25), including an additional step of denaturing the purified recombinant protein by using a reducing agent having an ability of reducing a disulfide bond before the refolding step;
(27) The method according to (25) or (26), including an additional step of purifying the refolded recombinant protein by a gel filtration column chromatography after the step of purifying the refolded recombinant protein by the anion exchange column chromatography;
(28) The method according to any one of (25) to (27), including an additional step of cross-linking the recombinant protein;
(29) The method according to any one of (25) to (28), wherein the refolding agent is selected from a group comprising: arginine, arginine amide, arginine ethyl ester, lysine, spermidine, spermine, guanidine, guanidine propionate, glycine, proline, urea, sucrose, glucose, N-acetylglucosamine, SDS, Tween 20, sodium sulfate, ammonium sulfate, ammonium iodide, ammonium thiocyanate, taurine, betaine, glycerol, polyol, β-alanine, trimethyl ammonium N-oxide, disaccharide, trehalose, polyethylene glycol, amino acid alkyl ester, amino acid amide, diamine, polyamine, imidazole and histidine;
(30) The method according to any one of (25) to (29), including a process for detecting a biologically active recombinant protein;
(31) The methods according to (30), wherein the detection of the biologically active recombinant protein is performed by a cross-linking reaction;
(32) The method according to any one of (1) to (31), wherein the recombinant protein is a recombinant IL-10 derived from a vertebrate selected from a group comprising: mammal, human, mouse, rat, guinea pig, hamster, rabbit, dog, cat, sheep, pig, cow and horse;
(33) The method according to (32), wherein the recombinant IL-10 is a recombinant hIL-10 derived from a human;
(34) A recombinant protein, wherein the content of endotoxin is 0.0001 EU/μg or less;
(35) A recombinant protein, wherein the content of endotoxin is 0.00001 to 0.00004 EU/μg;
(36) The recombinant protein according to (33) or (35), wherein the recombinant protein is a recombinant IL-10;
(37) The recombinant protein according to (34) or (35), wherein the recombinant protein is a recombinant hIL-10 derived from a human;
(38) DNA consisting of the gene sequence (SEQ ID NO: 1).

The present invention is partly described in the following publications published within one year prior to the present application: Fujiwara, et al., Protein Expression and Purification 72, 125-130 (2010) and Kokai Tokyo Koho JP 2010-183904 (not examined Japanese patent publication).

BRIEF DESCRIPTION OF THE DRAWINGS

The present invention is understood by the following figures, but not limited thereto.

FIG. 1: gene sequence (SEQ ID NO: 1) of hIL-10, wherein the codon of hIL-10 cDNA (accession number: BC 104252) was modified for the expression in rice, and the corresponding amino acid sequence (SEQ ID NO: 2).

FIG. 8: summary of the total seed proteins (mg), recombinant hIL-10 (mg), their recovery rate (%) and purity (%) in each purification steps in FIG. 6 based on the protein analysis measuring protein concentration in each samples.

DETAILED DESCRIPTION OF THE INVENTION

Figure 2:
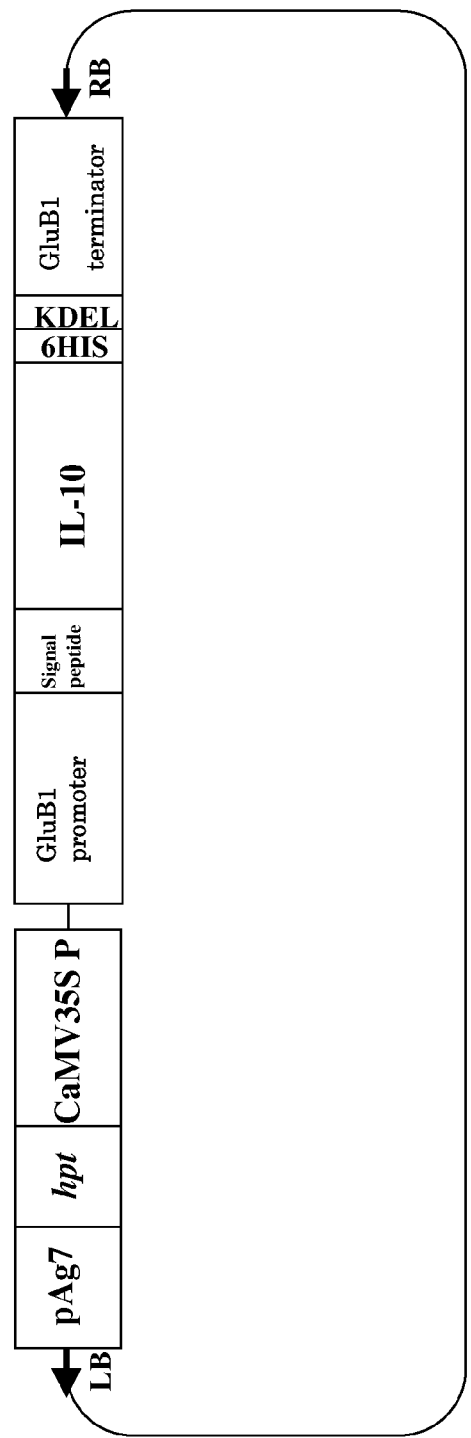
FIG. 2: schematic diagram of the expression vector for the rice transformation.

The present invention of a novel and practically efficient method for extracting and purifying recombinant proteins from transgenic plants, especially from the seeds 'of transgenic plants, wherein such recombinant proteins are at the state of difficulties in extracting by the general method, has been performed by using the combination of extractions: pre-extraction of plant proteins (for example, storage proteins containing a great deal of cysteine (prolamine, glutelin, etc.)) (occasionally referred to "pre-extraction" in the present invention) and extraction of recombinant proteins. The extraction of recombinant proteins can be performed by an extraction solution containing reducing agents and surfactants or by an extraction solution containing reducing agents and organic solvents.

There are recombinant proteins rendered difficult to extract from transgenic plants with buffer extraction solutions containing Tris or phosphoric acid and non-ionic surfactants commonly used in a general protein extraction. Whether easily water soluble or not, such recombinant proteins are rendered difficult to extract probably due to the following reasons: the recombinant proteins are encapsulated in an inclusion body or a protein body, the recombinant proteins are in an aggregated form, intra-molecular disulfide bonds (Cys-Cys) are formed in the recombinant proteins, inter-molecular non-covalent bonds are formed incorrectly among sub-units of the recombinant proteins, the recombinant proteins are bonded to plant proteins, or the state of recombinant proteins in the seeds of transgenic plants are changed during their storage.

One of examples of such recombinant proteins is recombinant IL-10. Recombinant IL-10 of the present invention is derived from vertebrates, preferably mammals, more preferably humans, mice, rats, guinea pigs, hamsters, rabbits, dogs, cats, sheep, pigs, and cows, as well as horses, etc., and particularly preferably from humans or mice, but not limited thereto.

The gene sequences and amino acid sequences of the recombinant proteins registered at GeneBank (US NCBI), etc can be used in the present invention. For example, recombinant human IL-10 (recombinant hIL-10) is registered at GeneBank as BC104252 and the genetic information thereof can be used in the present invention. The transgenic plants expressing the recombinant proteins can be prepared by using well-known transgenic methods (Toya Matsubayashi Ed. Watson/Molecular Biology of Recombinant DNA Rev. 2, 1994, Maruzen Experimental Protocols for Model Plants Rev. 3 (2005) Shimamoto, Okada, Tabatake Ed., Shujunsha). The transgenic plants are prepared by integrating the genes coding the recombinant proteins into expression vectors, and introducing the vectors into the target plant cells.

The genes of the present invention include mutations thereof (including analogues and homologues). "Mutation" herein refers to items in which one or multiple, or more preferably one or several, nucleotides are replaced, added or lost in the nucleotide sequences of the genes, or mutations thereof showing the homology of 70% or more of the normal nucleotide sequences, or preferably 80% or more, 85% or more, or more preferably 90% or more, and most preferably 95% or more, 98% or more, and 99% or more.

"Several" in the present invention indicates an integer around 10, 9, 8, 7, 6, 5, 4, 3 or 2. In addition, the "% homology" can be determined with or without introducing gaps by accessing the sequences database of GeneBank (US NCBI) and using homology search algorithms for nucleic acids and proteins such as BLAST and FASTA, and the like (Norihisa Takagi, Minoru Kanehisa, Genome Datanet Usage Methods (Rev. 2) 1998, Kyoritsu Shuppansha).

The gene sequences of the recombinant proteins can be modified in accordance with the codon frequency of the target plants for their transformation.

Vectors commonly known in this field can be used as the vectors in the present invention for introducing and expressing genes of the recombinant proteins herein, for example, pUC series vectors, pBR series vectors, pBI series vectors, pGA series vectors, etc. In addition, pBin19, pBI121, pGreen series, pCAMBIA series, pPZP series, pPCV001, pGA482, pCLD04541, pBIBAC series, pYLTAC series, pSB11, pSB1, and pGPTV series, etc. can be used as the binary vector for *agrobacterium*. Furthermore, it is also possible to use virus vectors and the like. Vectors in the present invention can suitably include, in addition to control sequences such as promoters, etc., signal sequences, tag sequences, protease recognition sequences, selection markers, and the like.

Promoters in the present invention are not specifically restricted, insofar as it is possible to drive the genetic expression within the plant cells, for example, cauliflower mosaic virus 35S promoter, rice acting gene promoter, glutelin promoter, and the like can be used. Tag sequences in the present invention are not specifically restricted insofar as it makes it possible to easily purify the expressed recombinant protein, for example, six repeated histidine, GST, MBP, HAT, HN, S, TF, Trx, Nus, biotin, FLAG, myc, RCFP, GFP and the like can be used. Protease recognition sequences in the present invention are sequences that recognize proteases for the purpose of removing tag sequences and unneeded sequences, and there are no particular restrictions insofar as these are sequences capable of fractioning proteases, and, for example, recognition sequences such as Factor Xa, Thrombin, HRV 3C protease, TEV protease, and the like can be used. Selection markers in the present invention are not specifically restricted insofar as they are capable of detecting transformed plant cells, and for example, neomycin resistance gene, kanamycin resistance gene, hygromycin resistance gene, and the like can be used. The transformation of plants, wherein the constructed expression vectors are used, can be performed by the commonly-known methods. For example, the *agrobacterium* method, electropolation method, micro-injection method, and particle gun method and the like can be performed. Although any monocotyledon or dicotyledon can be used as the plants for transformation in the present invention, plants that have long been eaten by humans are preferable. For example, though nor specifically limited to, tobacco, cabbage, lettuce, rice, potatoes, cucumbers, eggplants, tomatoes, barley, wheat, maize, rye, sorghum, rapeseed, cotton, mustard, *Arabidopsis thaliana*, sunflower, alfalfa, chickpeas, clover, peas, peanuts, yellow split peas, broad beans, *Medicago polymorpha*, cassava, water lentils, water hyacinth, citrus, peaches, as well as apples can be used as the plants for transformation in the present invention, and preferably grain plants, and most preferably rice plants.

"Plant protein" in the present invention indicates a protein produced by a plant and stored therein, wherein a recombinant protein is not included. The major storage proteins in the crop seeds of grain plants are prolamin, globulin, and glutelin, which are typical examples of plant proteins. The protein species and the component ratio of storage proteins are depending on the type of cereal seeds. Gluten and zein, which are members of prolamin family, are major components of wheat and corn storage proteins, respectively. Glycinin, which is a member of globulin family, is a major component of soybean storage proteins. Prolamin and glutelin are major components of rice storage proteins. Those storage proteins are accumulated in the protein body of the seeds and form a water insoluble complex by their intra-molecular disulphide bonds and/or inter-molecular non-covalent bonds (Shewry, et al., Journal of Experimental Botany, 53, 947-958 (2002)). Therefore the present invention fundamentally and preferably is used for the extraction and purification of recombinant proteins accumulated in the protein body of the cereal seeds of transgenic grain plants such as transgenic rice, wheat, corn and soybean plants.

The 'transgenic plants" in the present invention include the entire transgenic plants or part of the transgenic plants (for example, organs, tissues, seeds, callus, cells, or shoots, and the like). Preferably, the seeds of transgenic plants, more preferably the seeds of transgenic grain plants, and most preferably the seeds of transgenic rice plants can be used for the extraction and purification of recombinant proteins. The transgenic plants can be used preferably after pulverizing by the well-known methods, for example, pulverization by ultrasonic processing, French press, stone mill, mortar and pestle, homogenizer, and glass beads. The pulverization of transgenic plants is suitable for the effective extraction and purification of recombinant proteins.

The pre-extraction process can be performed by using, for example, 1 to 20 mL, preferably 2 to 10 mL, and more preferably 5 mL of an extraction solution for 1 g of pulverized transgenic plants or pulverized seeds of transgenic plants. The pre-extraction process for extracting plant proteins as contaminated proteins may be performed by using each extraction solution individually or an extraction solution combined different extraction solutions, and may be repeated.

Figure 3:
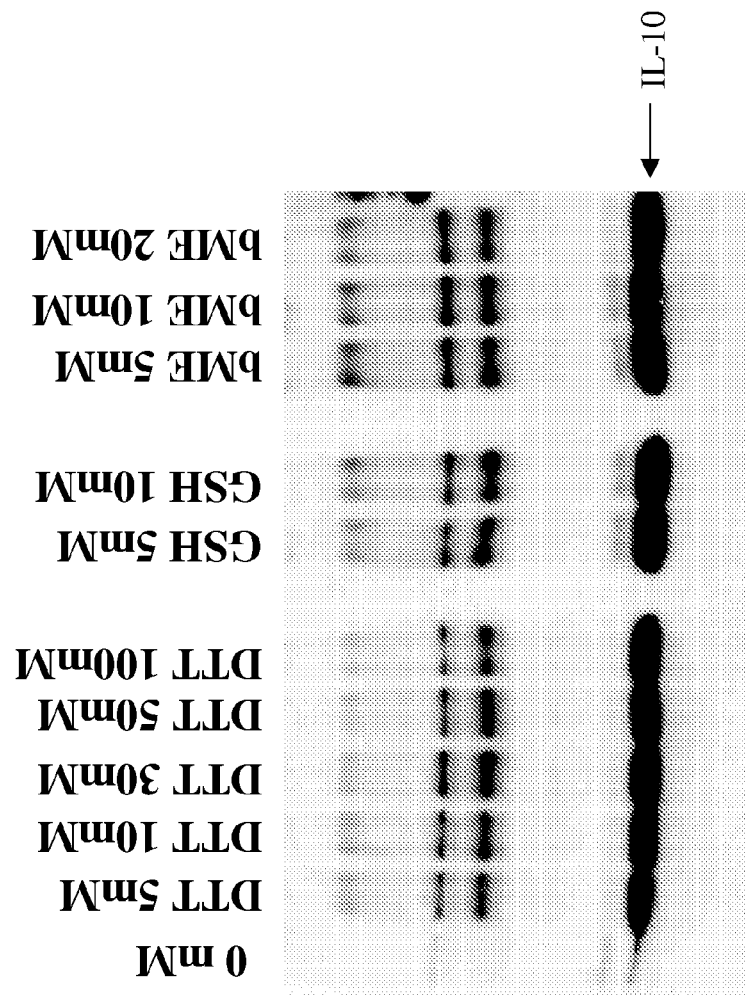
FIG. 3: results of recombinant hIL-10 extraction from the rice seeds of transgenic rice plants by changing the concentration of reducing agents in an extraction buffer solution. Extraction was performed by adding 1 mL of extraction buffer solution to 0.1 g of pulverized rice seeds (rice powder), wherein each extraction buffer solution was containing 50 mM Tris hydrogen chloride (Tris-HCl) (pH 7.4), 0.5 M NaCl, 1 wt % SB3-14 (surfactant) and reducing agents. Extracted samples were separated by sodium dodecyl sulfate-polyacrylamide gel electrophoresis (SDS-PAGE) and detected by the Western blotting method using anti-His tag antibodies.
Figure 4:
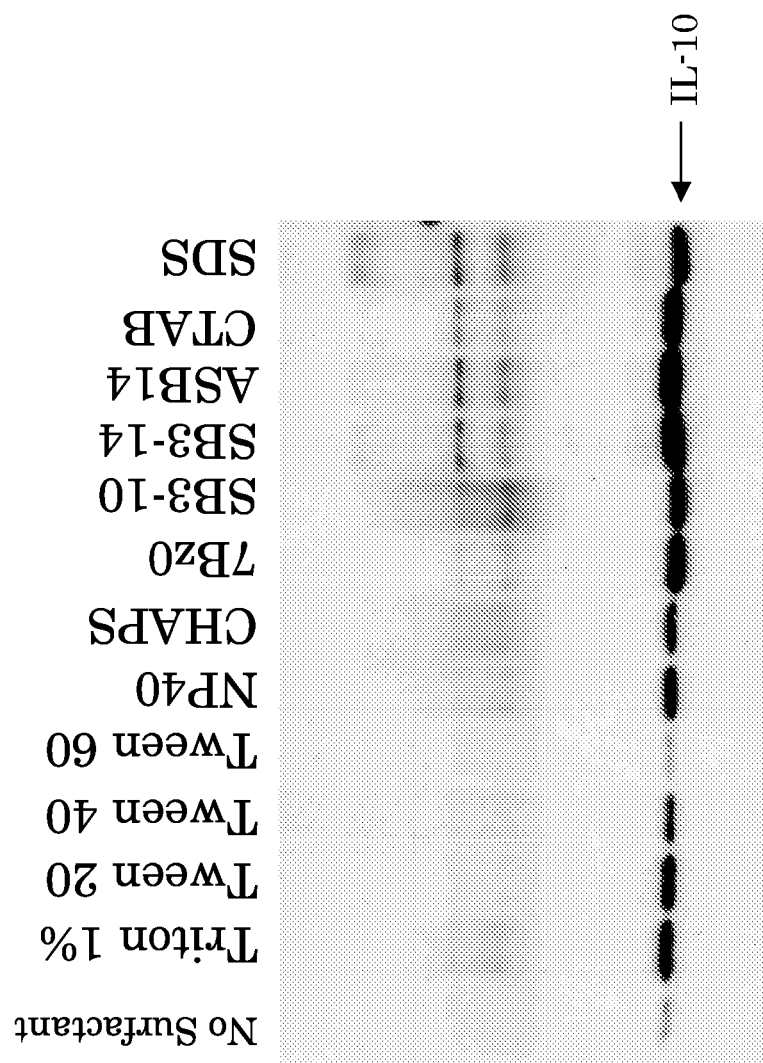
FIG. 4: results of recombinant hIL-10 extraction from the rice seeds of transgenic rice plants by changing the concentration of surfactants in an extraction buffer solution. Extraction was performed by adding 1 mL of extraction buffer solution to 0.1 g of pulverized rice and stirring overnight at 4° C., wherein the extraction buffer solution was containing 50 mM Tris-HCl (pH 7.4), 0.5 M NaCl and surfactants. Extracted samples were separated by SDS-PAGE and detected by the Western blotting method using anti-His tag antibodies.

(I) Pre-extraction of Plant Proteins and Extraction of Recombinant Proteins Using Extraction Buffer Solution Containing Reducing Agents and Surfactants The recombinant proteins which are at the state of difficulties in extracting can be effectively extracted from the pulverized transgenic plants by using an extraction buffer solution containing reducing agents and surfactants as shown in detail in Examples and FIGS. 3 and 4. The extraction of recombinant proteins can be performed under the following conditions.

General buffer solution can be used as the buffer solution for preparing the extraction buffer solution of the present invention, for example, buffer solution selected from Tris buffer solution, phosphoric acid buffer solution, Tricine buffer solution, Hepes buffer solution, MOPS buffer solution, carbonic acid buffer solution, citric acid buffer solution, boric acid buffer solution, MES buffer solution, and PIPES buffer solution, containing 100 to 700 mM, preferably 500 to 700 mM, and more preferably 500 mM NaCl, with pH 6 to 10, preferably pH 7 to 8, and more preferably pH 7.4.

General reducing agents having an ability of reducing disulfide bonds can be used as the reducing agents of the present invention, and, for example, such reducing agents can be selected from Dithiotbreitol (DTT), reduced Glutathione (GSH), β-mercaptoethanol (bME), TCEP (tris(2-carboxyethyl) phosphine hydrochloride), cysteine, 2-mercaptoethylamine and 3-mercaptopropionic acid, and preferably DTT and bME, and more preferably bME. The concentration of the reducing agents in the extraction buffer solution is 1 mM or higher, and preferably 5 mM or higher, and more preferably 10 mM or higher.

General surfactants can be used as the surfactants of the present invention, and, for example, such surfactants can be selected from non-ionic surfactants such as TritonX-100, NP-40 and Tween, zwitterionic surfactants such as 7BzO, SB3-10, SB3-14, CHAPS and Amidosulfobetaine-14 (ASB 14), and ionic surfactants such as Cetyl trimethylammonium bromide (CTAB) and sodium decyl sulfate (SDS), and preferably zwitterionic surfactants and ionic surfactants, and more preferably ionic surfactants, and further preferably ionic surfactants selected from CTAB and SDS, and even more preferably CTAB. The concentration of surfactants in the extraction buffer solution is 0.5 to 1.5 wt %, and preferably 0.5 to 1 wt %, and more preferably 1 wt %.

The extraction of recombinant proteins can be performed by using, for example, 5 to 50 mL, preferably 10 to 30 mL, and more preferably 20 mL of the extraction buffer solution containing the reducing agents and the surfactants for 1 g of pulverized transgenic plants.

The extraction of recombinant proteins can be performed by adding the extraction buffer solution containing reducing agents and surfactants to the pulverized transgenic plants, and stirring for several to 24 hours, preferably 8 to 12 hours at low temperature, for example, at 0 to 15° C., preferably at 4 to 10° C., and more preferably at 4° C. The extraction of recombinant proteins, if necessary, can be repeated, preferably twice.

The present invention can be performed preferably by using a combination of pre-extraction of plant proteins and extraction of recombinant proteins: pre-extraction of plant proteins as contaminated proteins other than recombinant proteins using an extraction solution without containing the reducing agents and surfactants and extraction of recombinant proteins using the extraction buffer solution containing the reducing agents and surfactants.

The pre-extraction is performed in order to extract and eliminate plant proteins as the contaminated proteins for effective extracting and purifying recombinant proteins from transgenic plants. The pre-extraction process can be performed by using, for example, 5 to 50 mL, preferably 10 to 30 mL, and more preferably 20 mL of an extraction solution for 1 g of pulverized transgenic plants by the method similar to the extraction of recombinant proteins set forth above. Namely, the extraction solution for pre-extraction is added to the pulverized transgenic plants, stirred and centrifuged. After the supernatant containing the plant proteins extracted by the pre-extraction is discarded, the resulting precipitate is extracted by using the extraction buffer solution containing reducing agents and surfactants for extracting recombinant proteins therein. Each extraction process may be repeated multiple times as needed.

The pre-extraction process can be performed by using an extraction solution containing urea or guanidine. There is a report on the extraction of the contaminated proteins from transgenic *E. coli* by using an extraction solution containing guanidine or urea (Sambrook, et al., Molecular Cloning 2001, Vol. 3, 15-52. The pre-extraction of the present invention can be performed by using an extraction solution containing, for example, 2 to 8 M, preferably 4 M of guanidine or urea, and preferably surfactants can be added to the extraction solution containing urea, wherein any of the surfactants set forth above can be used, and preferably SDS. The concentration of the surfactants in the extraction solution is 0.5 to 1.5 wt %, preferably 0.5 to 1 wt %, and more preferably 1 wt %. The pre-extraction process can be repeated multiple times, for example, twice or more, preferably 3 to 7 times, and more preferably 5 times.

There are prolamine, cysteine-rich prolamine (cys-prolamine), globulin, and glutelin as plant proteins, particularly seed proteins, more particularly rice seed proteins, which are contaminated proteins in transgenic plants for extracting recombinant proteins therefrom. The following are known extraction methods for such seed proteins: extraction of prolamine using an extraction solution containing 60 vol % n-propanol; extraction of cys-prolamine using an extraction solution containing 60 vol % n-propanol and 5 vol % bME; extraction of globulin using an extraction solution containing 0.5 M NaCl; extraction of glutelin using an extraction solution containing 1 vol % lactic acid after extraction using an extraction solution containing 0.5 M NaCl (Ogawa, et al., Plant Cell Physiol. 28, 1517-1527 (1987)).

The pre-extraction method of the present invention for extracting glutelin using an extraction solution containing acetone, NaCl and bME after pre-extraction using an extraction solution containing 0.5 M NaCl is much more efficient than the conventionally and commonly known extraction method. The extraction solution of glutelin is containing 10 to 40 vol %, preferably 20 vol % acetone, 0.2 to 1 M, preferably 0.5 M of NaCl, and 0.01 to 10 vol %, preferably 5 vol % bME.

(II) Pre-Extraction of Contaminated Proteins and Extraction of Recombinant Proteins Using Extraction Solution Containing Organic Solvents and Reducing Agents The recombinant proteins which are at the state of difficulties in extracting can be effectively extracted from the pulverized transgenic plants by using a combination of pre-extraction of plant proteins and extraction of recombinant proteins: pre-extraction of plant proteins using an extraction solution containing salts and extraction of recombinant proteins using an extraction solution containing organic solvents and reducing agents.

General salts, though not specifically limited thereto, preferably neutral salts such as NaCl can be used for the pre-extraction of plant proteins.

General organic solvents, preferably water-soluble organic solvents, more preferably water-soluble lower alkanol, though not specifically limited thereto, such as n-propanol, i-propanol, n-butanol, s-butanol and t-butanol preferably n-propanol and i-propanol, and more preferably n-propanol can be used for the extraction of recombinant proteins.

General reducing agents having an ability of reducing disulfide bonds, though not specifically limited thereto, such as DTT, GSH, bME, TCEP, cysteine, mercaptoethylamine and mercaptopropionate, preferably DTT and bME, and more preferably bME can be used for the extraction of recombinant proteins.

The pre-extraction of plant proteins using an extraction solution containing NaCl, as an example of salts, and extraction of recombinant proteins using an extraction solution containing n-propanol, as an example of organic solvents, and bME, as an example of reducing agents, can be performed in a similar manner set forth above under the following conditions.

The extraction solution for pre-extraction of plant proteins containing 0.1 to 1 M, preferably 0.2 to 0.7M, and more preferably 0.5M NaCl in water or a general buffer solution, for example, Tris buffer solution, phosphoric acid buffer solution, Tricine buffer solution, Hepes buffer solution, MOPS buffer solution, carbonic acid buffer solution, citric acid buffer solution, boric acid buffer solution, MES buffer solution, and PIPES buffer solution can be used. Such extraction solution containing NaCl may contain further materials set forth above for pre-extraction of plant proteins.

The extraction solution for extraction of recombinant proteins containing 20 to 80 vol %, preferably 30 to 60 vol %, and more preferably 60 vol % n-propanol, and 0.01 to 10 vol %, preferably 0.1 to 10 vol %, more preferably 1 to 10 vol %, and more preferably 5 vol % bME can be used. Such extraction solution containing n-propanol and bME may contain further 0.01 to 1 M, preferably 0.2 to 0.7M, and more preferably 0.5 M NaCl.

The pre-extraction process can be performed by using, for example, 1 to 20 mL, preferably 2 to 10 mL, and more preferably 5 mL of an extraction solution containing NaCl for 1 g of pulverized transgenic plants or pulverized seeds of transgenic plants by the method similar to the pre-extraction process set forth above. Namely, an extraction solution containing NaCl is added to the pulverized transgenic plants for pre-extraction, stirred and centrifuged. After the supernatant containing the plant proteins extracted by the pre-extraction is discarded, the resulting precipitate is extracted by using the extraction solution containing n-propanol and bME for extracting recombinant proteins therein. Each extraction process may be repeated multiple times as needed.

The combination of pre-extraction of plant proteins (for example, extraction of prolamine using an extraction solution containing 60 vol % n-propanol; extraction of cys-prolamine using an extraction solution containing 60 vol % n-propanol and 5 vol % bME; extraction of glutelin using an extraction solution containing 1 vol % lactic acid after extraction using an extraction solution containing 0.5 M NaCl or extraction solution containing acetone, NaCl and bME after pre-extraction using an extraction solution containing 0.5 M NaCl) and extraction of recombinant proteins using an extraction solution containing n-propanol and bME can be performed in a similar manner as set forth above.

The recombinant proteins obtained by the combination of pre-extraction and the extraction using the extraction solution containing n-propanol and bME are pure enough for a refolding process without further purification or extraction, such as extraction using an extraction solution containing reducing agents and surfactants.

The refolding process may be performed in order to obtain a biologically active form of recombinant proteins by rewinding a biologically inactive form of denatured recombinant proteins to a biologically active form of their native structures. Such biologically inactive form is caused, for example, by the reduction of intra- or inter-molecular disulfide bonds of recombinant proteins during the extraction process thereof using an extraction solution containing reducing agents.

IL-10, as an example of such recombinant proteins, has two sets of intra-molecular disulfide bonds in its monomer form and the disulfide bonds act to maintain the spatial protein structure thereof. Two monomers of IL-10 are bonded each other by a noncovalent bond to form a homodimer thereof, which is a biologically active form of its native structure. Such non-covalent bond may be destroyed by surfactants set forth above. If these bonds are destroyed, IL-10 becomes irreversibly denatured and lose its biologically activity. Therefore, the refolding process is necessary to obtain a biologically active form of native structure in the case that recombinant proteins are denatured during the pre-extraction process of plant proteins and/or the extraction process of recombinant proteins.

Further purification of extracted recombinant proteins may be performed prior to the refolding process, if necessary, to remove contaminated surfactants, plant proteins and other impurities therefrom. The purification can be performed by a general purification method such as affinity chromatography, ion exchange chromatography, size exclusion chromatography, hydrophobic interaction chromatography, immobilized metal affinity chromatography, hydroxyapatite chromatography or suitable combination thereof. Preferably, the purification can be performed by using an affinity column chromatography recognizing the tag proteins of recombinant proteins derived from marker genes. The purification process can be repeated multiple times, and preferably twice, as needed. In addition, protein aggregation inhibitors, which can prevent recombinant proteins from aggregating, for example, guanidine hydrochloride, and the like, may be preferably used in the purification process thereof.

The refolding and denaturing processes of the present invention can be performed by a general method in this field, and preferably the denaturing process is performed prior to the refolding process in order to perform the refolding process effectively. The denaturing process can be performed as follows: aggregated or erroneously folded recombinant proteins are dissolved in a buffer solution containing denaturing agents, for example reducing agents having an ability of reducing disulfide bonds, and preferably containing denaturing agents and protein aggregation inhibitors. General buffer solutions, though not specifically limited thereto, such as Tris, Hepes, Tricine buffer solution and the like, containing 2 to 7 M, and preferably 6 M protein aggregation inhibitors such as guanidine hydrochloride, and 20 to 50 mM, and preferably 30 mM general reducing agents having an ability of reducing disulfide bonds, such as, though not specifically limited thereto, DTT, GSH, bME and the like, and preferably DTT can be used as the denaturing buffer solutions in the denaturing process. Boric acid is not preferable as such buffer solutions. The higher the concentration of recombinant proteins in such buffer solutions, the better the results, and preferably 1 mg/ml to 100 mg/ml, and more preferably 20 mg/ml to 50 mg/ml recombinant proteins. The higher the purity of recombinant proteins, the better the results, and preferably 80 to 100%, more preferably 90 to 100%, and even more preferably 95 to 100% purity of recombinant proteins. The denaturing temperature can be suitably selected from a range of room temperature to around 50° C., preferably 10 to 30° C., and more preferably 20 to 25° C. The denaturing time can be suitably selected in a range of 0.5 to 24 hours, preferably 1 to 6 hours, and more preferably 2 to 4 hours.

General buffer solutions, though not specifically limited thereto, such as Tris, Hepes, Tricine buffer solution and the like containing 0.2 to 2 mM, and preferably 0.5 mM oxidizing agents having an ability of oxidizing thiol group (for example, oxidizing cysteine moiety in the recombinant proteins to cystine moiety) and 0.1 to 2 M and preferably 0.6 M refolding agents, which can promote refolding of extracted recombinant proteins to the active form of native structure, can be used as the refolding buffer solutions in the refolding process. Boric acid is not preferable as such buffer solutions.

General oxidizing agents, though not specifically limited thereto, such as oxidized glutathione, cystine and the like, and preferably oxidized glutathione can be used as the oxidizing agents in the refolding process.

General refolding agents, though not specifically limited thereto, such as arginine, arginine amide, arginine ethyl ester, lysine, spermidine, spermine, guanidine, guanidine propionate, glycine, proline, urea, sucrose, glucose, N-acetylglucosamine, SDS, Tween 20, sodium sulfate, ammonium sulfate, ammonium iodide, ammonium thiocyanate, taurine, betaine, glycerol, polyol, β-alanine, trimethyl ammonium N-oxide, disaccharide, trehalose, polyethylene glycol, amino acid alkyl ester, amino acid amide, diamine, polyamine, imidazole, histidine and the like can be used as the refolding agents in the refolding process. Preferably, refolding agents selected from a group comprising arginine and derivatives thereof such as arginine ethyl ester, arginine amide and the like, which are known as inhibitors of protein aggregation, can be used.

The refolding process can be effectively performed by diluting the concentration of denatured recombinant proteins in the refolding buffer solution, preferably by diluting the denaturing buffer solution containing denatured recombinant proteins with the refolding buffer solution, wherein the dilution ratio is 10 to 50 times or more, preferably 70 times or more, more preferably 90 times or more, and most preferably 100 times or more. The refolding process can be performed in an alkaline buffer solution, preferably in pH 8 to 9 buffer solution. The reaction temperature thereof can be suitably selected in a range of 4 to 50° C. and preferably. The reaction time thereof can be suitably selected in a range of 3 to 24 hours, and preferably 8 to 12 hours.

The refolding process can be also performed by a general dialyzing method.

The recombinant proteins obtained by the refolding process can be purified by the general purification method in this field, though not specifically limited thereto, such as affinity chromatography, ion exchange chromatography, size exclusion chromatography, hydrophobic interaction chromatography, immobilized metal affinity chromatography, hydroxyapatite chromatography and the combinations thereof.

The non-covalent homodimer of recombinant IL-10, as an example of recombinant proteins, obtained by the refolding process is purified preferably by using an anion exchange column chromatography. Such homodimer form of recombinant IL-10 can be absorbed to the anion exchange resin in a pH 8.5 to 10.0, preferably pH 9.0 buffer solution, and can be eluted by a pH 9.0 buffer solution containing salts, preferably by pH 9.0 Tris buffer solution containing NaCl. The elution can be preferably performed by the general gradient method with a linear gradient from 0 to 0.5 M NaCl. The homodimer of recombinant IL-10 can be subsequently purified as needed by the general purification method, though not specifically limited thereto, such as affinity chromatography, ion exchange chromatography, size exclusion chromatography, hydrophobic interaction chromatography, immobilized metal affinity chromatography, and hydroxyapatite chromatography and combinations thereof.

The present invention further includes a process of detecting a biologically active form of recombinant proteins by the evaluation of the biological activity thereof and the analysis thereof by either the SDS-PAGE or Western blot method. A biologically inactive form of IL-10, as an example of recombinant proteins, has a molecular weight of 20 kDa as a monomer, while a biologically active form of IL-10 has a molecular weight of 40 kDa as a dimmer. Therefore, the biologically active form of recombinant IL-10, as an example of recombinant proteins, can be easily detected by either the SDS-PAGE or Western blot method combining with a general cross-linking method using cross-linking agents.

General cross-linking agents, though not specifically limited thereto, such as Bis (sulfoxine imidine) (sperate (BS3), Sulfo-EGS (ethylene glycol bis[sulfoxine imidyl succinate]), DTSSP (3,3'-dithiobis[sulfoxine imidyl propionate]), DTBP (dimethyl 3,3'-dithio bis propionimidate 2 HCL), DMS (dimethyl suberiimdate), DMP (dimethyl adipimidate), DMA (dimethyl adipimidate 2 HCL) and the like can be used as the cross-linking agents in the present invention, and the cross-linking reaction using such cross-linking agents can be performed in a similar manner as described in a published document (Systo, et al., Biochemistry 37, 16943-51. (1998)).

The recombinant IL-10, as an example of recombinant proteins, obtained as a biologically active dimmer form of IL-10, has a biological activity equivalent to its native IL-10. The biological activity can be evaluated by a general IL-10 bioassay method based on the inhibition activity of the production of IL-12p70 which is produced by LPS stimulation of the bone marrow-derived dendric cells. "Equivalent" herein means 80% or more of the activity of its native IL-10, and preferably 90% or more, and even more preferably 99% or more.

Endotoxin Free Recombinant hIL-10

Endotoxins are lipopolysaccharides, which are components of cell wall of gram negative bacteria. Endotoxins bind to Toll Like Receptor-4 (TLR-4) on macrophages, and induce production of inflammatory cytokines. Endotoxins are categorized as pyrogen. Although approval of pharmaceuticals are required pyrogen free, the recombinant proteins produced by the general method using *E. coli*. are inevitably contaminated with considerable amount of endotoxins (Magalhaes et al., J. Pharm. Pharm. Sci. 10, 388-404 (2007); Hirayama et al., J. Chromatogr. B Analyt. Technol. Biomed. Life Sci. 781, 419-432 (2002)), and thus removal of endotoxin from the recombinant proteins is essential but costly. FDA (Food and Drug Administration, USA) made regulations on pyrogen content in pharmaceuticals as the level that does not induce fever if administered to healthy person.

The present invention enables to produce recombinant hIL-10, as an example of recombinant proteins, from the pulverized rice seeds of transgenic rice plants at extremely low level of endotoxin (0.00001 to 0.00004 EU/µg) by the extraction and purification methods set forth above using freshly prepared ultra pure water which is free of endotoxin and glassware which is dry-heated before using to decompose any endotoxins therein. Ultra pure water (MilliQ water) is prepared by using Milli-Q SP TOC system with millipak express 40 filter (Millipore, Bedford, Mass.). Namely, further process to remove endotoxin from the products obtained is unnecessary in the present invention, if the extraction and purification procedures are performed carefully to prevent contamination from the water and apparatus used for extraction and purification of recombinant hIL-10.

The "endotoxin free" in the present invention means extremely low level of endotoxin (0.0001 EU/μg or less), which is measured by the *Limulus amebocyte* lysate method using an Endospecy ES-24S kit with an EG reader SV-12 (Seikagaku Biobusiness Co., Tokyo, Japan) according to the manufacturer's instructions. The endotoxin content in the recombinant hIL-10 produced by the present invention is approximately 1/10,000 to 1/100,000 of that in commercially available hIL-10 produced by using bacteria (0.1 to 1 EU/μg). Cytokine with this extremely low level of endotoxin has not been available until the present invention. Therefore, recombinant hIL-10 of the present invention, wherein endotoxin level is 0.0001 EU/μg or less, preferably 0.00001 to 0.00004 EU/μg, is obviously novel and distinguished from any known recombinant hIL-10 which has been produced by other methods until the present invention.

Recombinant IL-10, which are derived from vertebrates, mammals, humans, mice, rats, guinea pigs, hamsters, rabbits, dogs, cats, sheep, pigs, cows and horses, and wherein the concentrations of endotoxin is extremely low level such as 0.00001 to 0.00004 EU/μg or 0.00001 EU/μg or less, can be produced by the methods set forth above or by the modified methods thereof from transgenic plants, transgenic monocotyledon and dicotyledon plants that have long been eaten by humans such as tobacco, cabbage, lettuce, rice, potatoes, cucumbers, eggplants, tomatoes, barley, wheat, maize, rye, sorghum, rapeseed, cotton, mustard, *Arabidopsis thaliana*, sunflower, alfalfa, chickpeas, clover, peas, peanuts, yellow split peas, broad beans, *Medicago polymorphs*, cassava, water lentils, water hyacinth, citrus, peaches and apples, organs, tissues, seeds, callus, cells and shoots of transgenic plants, cereal seeds of transgenic grain plants, seeds of rice, wheat, corn and soybean, and is also obviously novel and distinguished from any known recombinant IL-10 which has been produced by other methods until the present invention.

As the non-covalent homodimer of recombinant IL-10 obtained by the present invention is very pure and safe, it is highly expected to contribute to various fields such as research fields, clinical fields and the like.

The following are EXAMPLES of the present invention, however, the present invention is not limited thereto.

EXAMPLE 1

Generation of Transgenic Rice Plants Expressing Recombinant hIL-10

In order to express recombinant hIL-10 in rice seeds, vectors expressing recombinant genes using a glutelin promoter were used. (Yang, et al., Plant Biotechnol. J. 5, 815-26. (2007); Kokai Tokkyo Koho JP 2008-109946). The secretion signal is removed from hIL-10 gene based on the genetic sequencing information of hIL-10 (Gene Bank registration number: BC 104252), and the codon of hIL-10 was converted to a rice-type codon according to the codon frequency of rice seed proteins. The resulting novel nucleotide sequence (SEQ ID NO: 1) of the hIL-10 gene, wherein the codon is converted to a rice-type codon, and the corresponding amino acid sequence (SEQ ID NO: 2) are shown in FIG. 1. The 6His tag and the endoplasmic reticulum retention signal (KDEL), which increases recombinant protein accumulation in rice seeds (Yang, et al., Plant Biotechnol. J. 5, 815-826 (2007)), are attached to the 3' terminus of the nucleotide sequence, and jointed to the *agrobacterium* expression vector. pGPTV-355-HPT-GluB1T (Goto, et al., Nature Biotechnol. 17, 282-286 (1999)) was used as the *agrobacterium* expression vector containing a glutelin promoter (GluB-1 P), secretion signal and glutelin terminator (GluB-1 T). The hIL-10 gene was ligated downstream of the 2.3 kb GluB-1 P (Qu, et al., Plant Biotechnol. J. 2, 113-125 (2004)) containing a signal peptide sequence. The promoter and hIL-10 gene were ligated to the binary vector pGPTV-35S-HPT-GluB-1T (Yang, et al., Plant Biotechnol. J. 5, 815-826 (2007)). The expression construct was introduced into the rice genome (*Oryza sativa* cv. Kitaake) using the *Agrobacterium tumefaciens* mediated transformation method and the resulting transgenic rice plants were selected (Goto, et al., Nature Biotechnol. 17, 282-286 (1999)).

FIG. 2 shows the structure of this expression vector, which was prepared by using general and commonly known genetic technologies in this field. The hIL-10 gene was expressed specifically in the endosperm of the rice seeds due to being linked downstream of the glutelin promoter.

The transgenic rice plants were generated by a super highspeed transformation method via *agrobacterium* (Toki, et al., The Plant Journal 47, 969-976 (2006); Kokai Tokkyo Koho JP 2001-29075). The expression vectors constructed as per the above were introduced to *Agrobacterium tumefaciens* (*A. tumefaciens*) strain EHA 105 by the electroporation method. Mature rice (*Oryza sativa* cv Kitaake) seeds 4 to 5 days after seeding were processed over three days at 25° C. with the transformed *A. tumefaciens*. The infected seeds were continuously cultured over two weeks at 30° C. in an N6 selection medium containing hygromycin and then four weeks at 28° C. in an MS regeneration medium by using the general and commonly known genetic technologies in this field, and the seedlings reproduced from the derived callus were transferred to a greenhouse and were grown therein at 28° C. under the condition of 12 hours light/dark cycle to generate the transgenic rice plants expressing recombinant hIL-10 in the rice seeds thereof.

EXAMPLE 2

Pre-Extraction and Extraction of Recombinant hIL-10 Using Extraction Buffer Solution Containing Reducing Agents and Surfactants (1) Pre-Extraction of Contaminated Materials Other than Recombinant hIL-10

The rice seeds containing recombinant HIL-10 were collected from the transgenic rice plants generated in EXAMPLE 1. A 50 g of rice seeds was hulled to remove the hulls thereof and pulverized with an electric mill (SAMAP Corporation, F-50) to a fine powder thereof. To remove bran and germ and to collect albumen portion the pulverized rice seeds were screened at an aperture size of 355 μm. A 40 g of the resulting pulverized rice seeds was added to 800 mL of extraction buffer solution consisting of 50 mM Tris buffer solution (Tris-HCl, pH 7.4) and 0.5 M NaCl in a 1 L flask, and extracted overnight at 4° C. at 400 rpm using a magnetic stirrer. Contaminated materials including seed proteins other than recombinant hIL-10 in the pulverized rice seeds were extracted (FIGS. 3 and 4).

(2) Extraction of Recombinant hIL-10

Figure 5:
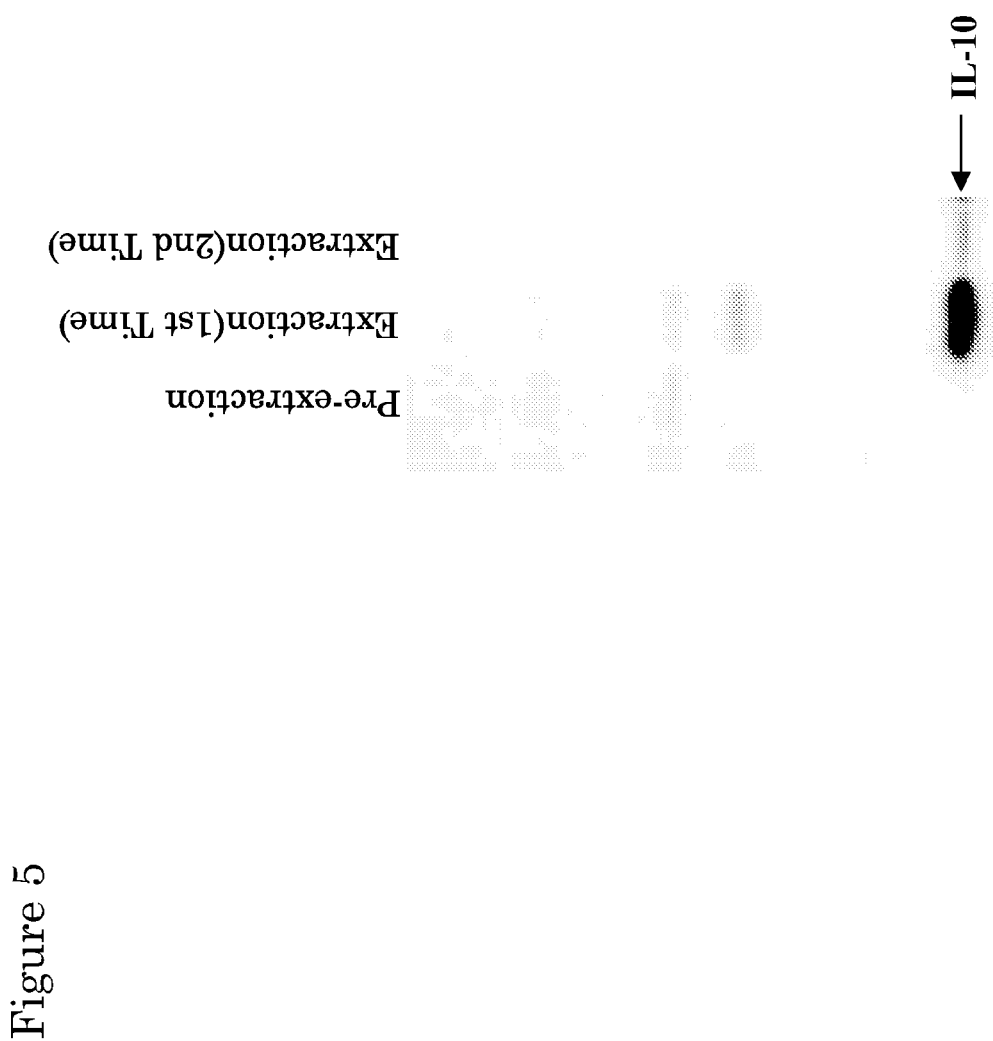
FIG. 5: results of pre-extraction of plant proteins and extraction of recombinant hIL-10 from the rice seeds of transgenic rice plants. Pre-extraction was performed by adding 1 mL of extraction buffer solution, which was containing 50 mM Tris-HCl (pH 7.4) and 0.5 M NaCl, to 0.1 g of pulverized rice seeds and stirring overnight at 4° C. The resulting precipitate was further extracted by an extraction buffer solution containing 50 mM Tris-HCl (pH 7.4), 0.5 M NaCl, 10 mM dithiothreitol (DTT) as reducing agents and 1 wt % surfactants. Extracted sample was separated by SDS-PAGE and detected by the Western blotting method using anti-His tag antibodies.

After pre-extraction, the resulting extraction buffer solution is centrifuged at 14,000 G for 10 minutes and the supernatant was removed. The resulting precipitate was extracted with 800 mL of the extraction buffer solution consisting of 50 mM Tris buffer solution (Tris-HCl, pH7.4), 0.5 M NaCl, 10 mM bME and 1 wt % CTAB for six hours at 4° C. using a magnetic stirrer in the same manner as above. The resulting supernatant is collected after being centrifuged at 1,500 G for 10 minutes and was extracted again with the same extraction buffer solution in the same manner as above. The resulting supernatant was placed in an ice for up to two hours, and the precipitated CTAB was removed by centrifugation at 10,000 G for 10 minutes and filtration with a glass filter (Whatman, GF/A) to afford the recombinant hIL-10 in the extraction buffer solution (FIG. 5).

EXAMPLE 3

Purification of Recombinant hIL-10

(1) First Purification of Recombinant hIL-10 by Ni Affinity Column

Figure 7:
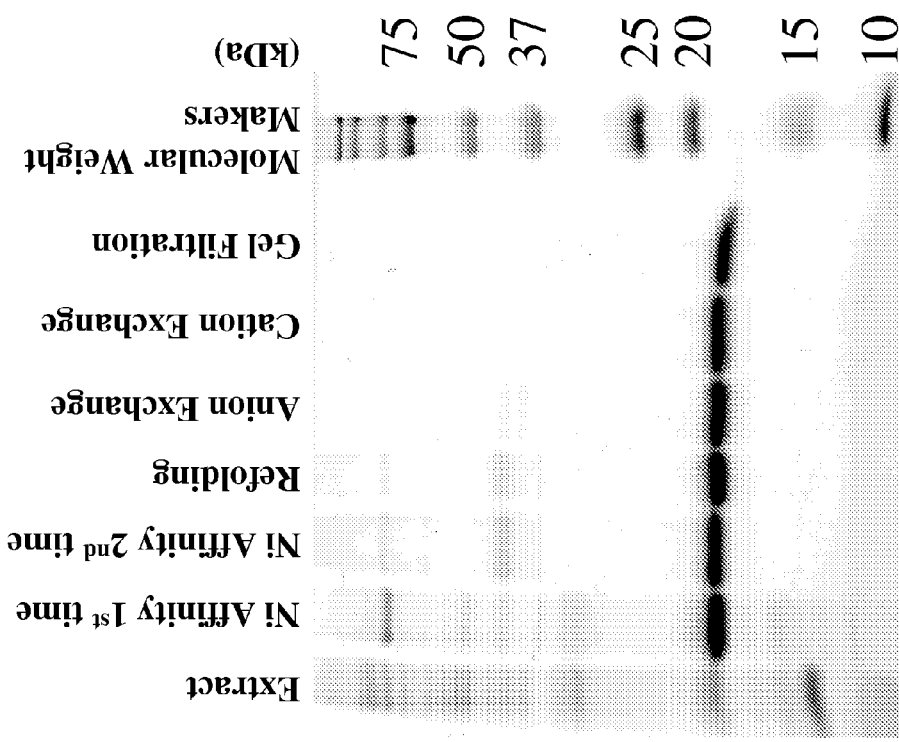
FIG. 7: results of staining with Coomassie brilliant blue (CBB) instead of Western blotting method using anti-His tag antibodies.

The resulting recombinant hIL-10 in the extraction buffer solution prepared in EXAMPLE 2 was purified by Histidine tag affinity column chromatography using HisTrap FF column 5 mL (GE Healthcare: AKTA prime plus) (Ni Affinity Column), which was performed by a general and commonly known purification method in this field. The recombinant hIL-10 was eluted by a stepwise elution method using a starting buffer solution (50 mM Tris-HCl (pH 7.4), 0.5 M NaCL, and 20 mM imidazole), an elution buffer solution (50 mM Tris-HCl (pH7.4), 0.5 M NaCl, and 0.4 M imidazole) (FIG. 7).

(2) Second Purification of Recombinant hIL-10 by Ni Affinity Column

The eluted fluid obtained from the first purification of recombinant hIL-10 by Ni affinity column was precipitated by adding acetone thereto. The resulting precipitate was dissolved in a starting buffer solution (20 mM Na phosphate (pH 7.4), 0.5 M NaCl, 20 mM imidazole, 10 mM bME, and 6M guanidine hydrochloride) and purified by eluting with elution buffer solution (20 mM Na phosphate (pH 7A), 0.5 M NaCl, 0.4 M imidazole, and 6M guanidine hydrochloride) using 1 mL of HisTrap FF column (GE Healthcare). The eluate containing recombinant hIL-10 was dialyzed in 10 mM Tris buffer solution (Tris-HCl, pH 7.4) to remove guanidine hydrochloride therein and recombinant hIL-10 was precipitated by adding acetone thereto (FIG. 7).

(3) Denaturing and Refolding of Recombinant hIL-10

The resulting precipitate of recombinant hIL-10 was dissolved in a denaturing solution (50 mM Tris-HCl (pH 8.5), 6 M guanidine HCl and 30 mM DTT) and placed for three hours at room temperature for denaturing of recombinant hIL-10. The resulting mixture was diluted with 50 fold volume of refolding buffered solution (50 mM Tris-HCl, (pH 8.5), 0.5 mM oxidized glutathione, 0.6 M arginine hydrochloride) and placed overnight at 33 to 42° C. for refolding of recombinant hIL-10.

Figure 6:
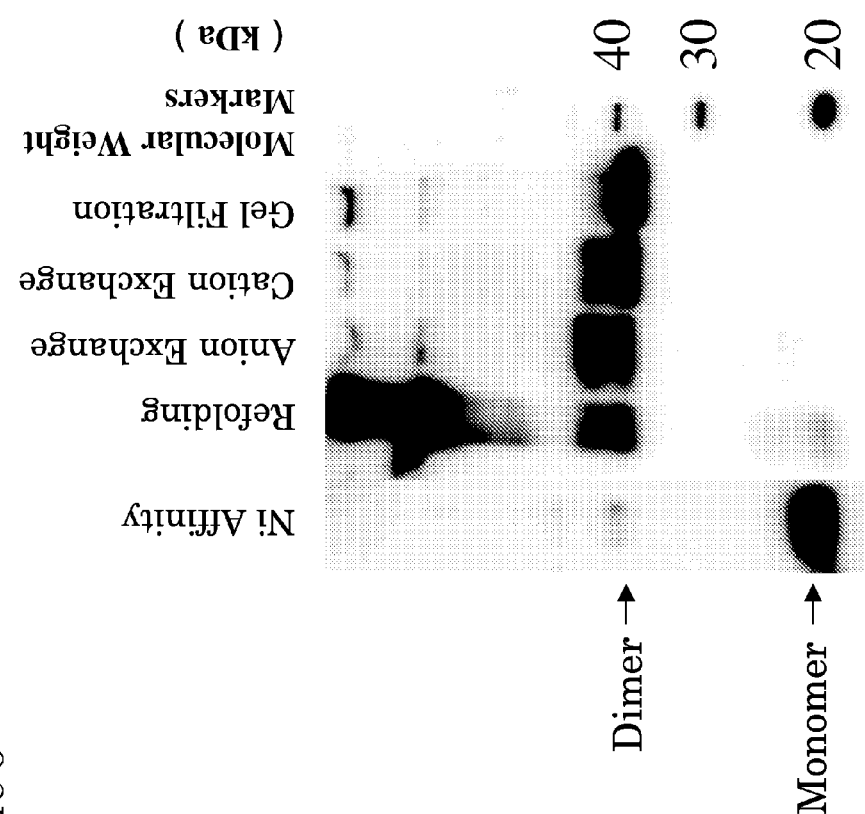
FIG. 6: non-covalent homodimer of recombinant hIL-10 in a series of purification steps after pre-extraction and extraction of recombinant hIL-10 from the rice seeds of transgenic rice plants: purification by HisTrapFF column, refolding by glutathione disulfide (oxidized glutathione) as refolding agents, and purification by column chromatography (anion exchange column, cation exchange column, gel filtration column). Purified samples were cross-linked by bis(sulfosuccinimidyl) suberate (BS3) as cross-linking agents, separated by SDS-PAGE and detected by the Western blotting method using anti-His tag antibodies.

Evaluation of the state of refolding was performed by detecting the homodimer of recombinant hIL-10 using sodium dodecyl sulfate-polyacrylamide gel electrophoresis (SDS-PAGE) and Western blotting method (Syto, et al., Biochemistry 37, 16943-51. (1998); Laemmli, Nature 227, 680-685 (1970); Burnett, Analyt. Biochem. 112, 195-203 (1981).) after cross-linking reaction thereof. A sample containing recombinant hIL-10, which was obtained by denaturing and refolding process, was dialyzed in PBS (1.5 mM potassium dihydrogenphosphate, 2.7 mM di-sodium hydrogenphosphate, 154 mM sodium chloride, pH 7.2). The resulting 10 μL (hIL-10 concentration: 0.1 mg/mL or less) of sample was mixed with 10 μL of a 0.4M sodium. bicarbonate buffer solution (PH 8.5) containing 2 mM BS3, and the cross-linking reaction was performed for 30 minutes at room temperature. Thereafter, the cross-linking reaction was quitted by the addition of 1 μL of 1 M Tris buffer solution (pH 8.0). By detecting the homodimer of recombinant hIL-10 in a sample thereof after cross-linking reaction using SDS-PAGE and the Western blot method, it was confirmed that refolding of recombinant hIL-10 was effectively performed (FIGS. 6 and 7).

(4) Purification by Anion Exchange Column

The resulting refolded recombinant hIL-10 in the refolding buffered solution was dialyzed over two days in PBS and 50 mM Tris-HCl (pH 9.0), subsequently. If precipitate was generated, it was removed by centrifuging, and the resulting supernatant was purified by an anion exchange column HiTrapQ 5 mL (GE Healthcare). It was eluted by the gradient elution method using a starting buffer solution (50 mM Tris (pH 9.0)) and an elution buffer solution (50 mM Tris-HCl (pH 9.0), 0.5 M NaCl). The eluate containing refolded recombinant hIL-10 was cross-linked in the same manner as above, and it was confirmed by using SDS-PAGE and the Western blotting method in the same manner as above that the homodimer of recombinant hIL-10 was effectively prepared (FIGS. 6 and 7).

(5) Purification by Cation Exchange Column

The resulting eluate containing refolded recombinant hIL-10, which was purified by an anion exchange column, was purified further by a cation exchange column in order to concentrate the fractions containing refolded recombinant hIL-10 and remove the trace amounts of remaining impurities therein. The eluate containing the homodimer of recombinant hIL-10 was dialyzed in 50 mM MES (pH 6.5), and purified by a cation exchange column HiTrapSP 1 mL (GE Healthcare). It was eluted by the gradient elution method using a starting buffer solution (50 mM MES (pH 6.5)) and an elution buffer solution (50 mM MES (pH 6.5), 0.5 M NaCl). The eluate containing refolded recombinant hIL-10 was cross-linked in the same manner as above, and it was confirmed by using SDS-PAGE and the Western blotting method in the same manner as above that the homodimer of recombinant hIL-10 was effectively prepared (FIGS. 6 and 7).

(6) Purification by Gel Filtration Column

The resulting eluate containing the homodimer of recombinant hIL-10, which was purified by a cation exchange column as above, was purified further by a gel filtration column in order to remove the trace amounts of remaining monomer of recombinant hIL-10. Purification by a gel filtration column was performed by the column of HiPrep 16/60 Sephacryl S-I00HR (GE Healthcare) using a 50 mM phosphoric acid buffer solution (pH 7.4) containing 150 mM NaCl. The eluate containing refolded recombinant hIL-10 was cross-linked in the same manner as above, and it was confirmed by using SDS-PAGE and the Western blotting method in the same manner as above that the homodimer of recombinant hIL-10 was effectively prepared (FIGS. 6 and 7).

(7) Protein Analysis

The protein samples of purified IL-10 and each purification stage were analyzed by using SDS-PAGE. After electrophoresis, the gels were stained with Coomassie brilliant blue (CBB) or transferred to polyvinylidene difluoride membranes (Immun-Blot, BioRad, Hercules, Calif.). The membranes were incubated with the anti-His tag antibodies (Roche Diagnostics GmbH, Mannheim, Germany) and then a peroxidase-conjugated secondary antibody (Dako Denmark A/S, Glostrup, Denmark). Alternatively, the membranes were stained by kits based on Periodic acid-Schiff (G.P. SENSOR, J-Oil Mills, Inc., Tokyo, Japan) or lectin (HRP-Lectin Kit, J-Oil Mills) methods. The signals were visualized by an ECL Plus Western blotting detection system (GE Healthcare UK Ltd., Little Chalfont Buckinghamshire, England) and the images were captured by using Chemi Doc XRS (Bio-Rad). Total protein concentration was measured by using either a standard BCA protein assay kit or reducing agent-compatible BCA protein assay kit (Thermo Scientific, Rockford, Ill.) with bovine serum albumin as the standard. The concentration of recombinant hIL-10 was measured by a hIL-10 instant enzyme linked immunosorbent assay kit (Bender Med Systems, Vienna, Austria) or Western blotting method. The results of protein analysis in each of the above purification stages are shown in FIG. 7, and the data on the recovery rate and purity of recombinant hIL-10 are shown in FIG. 8. Thus, it was confirmed that the recombinant hIL-10 was purified to a purity of 98% or higher by SDS-PAGE and reverse-phase column chromatography, and a 2.1 mg of active non-covalent dimer of purified recombinant hIL-10 was obtained from 40 g of pulverized rice seeds at a recovery rate of 4.3% from the total amounts of recombinant hIL-10 in the pulverized rice seeds.

(8) Measurement of Biological Activity and Endotoxin Level

Figure 9:
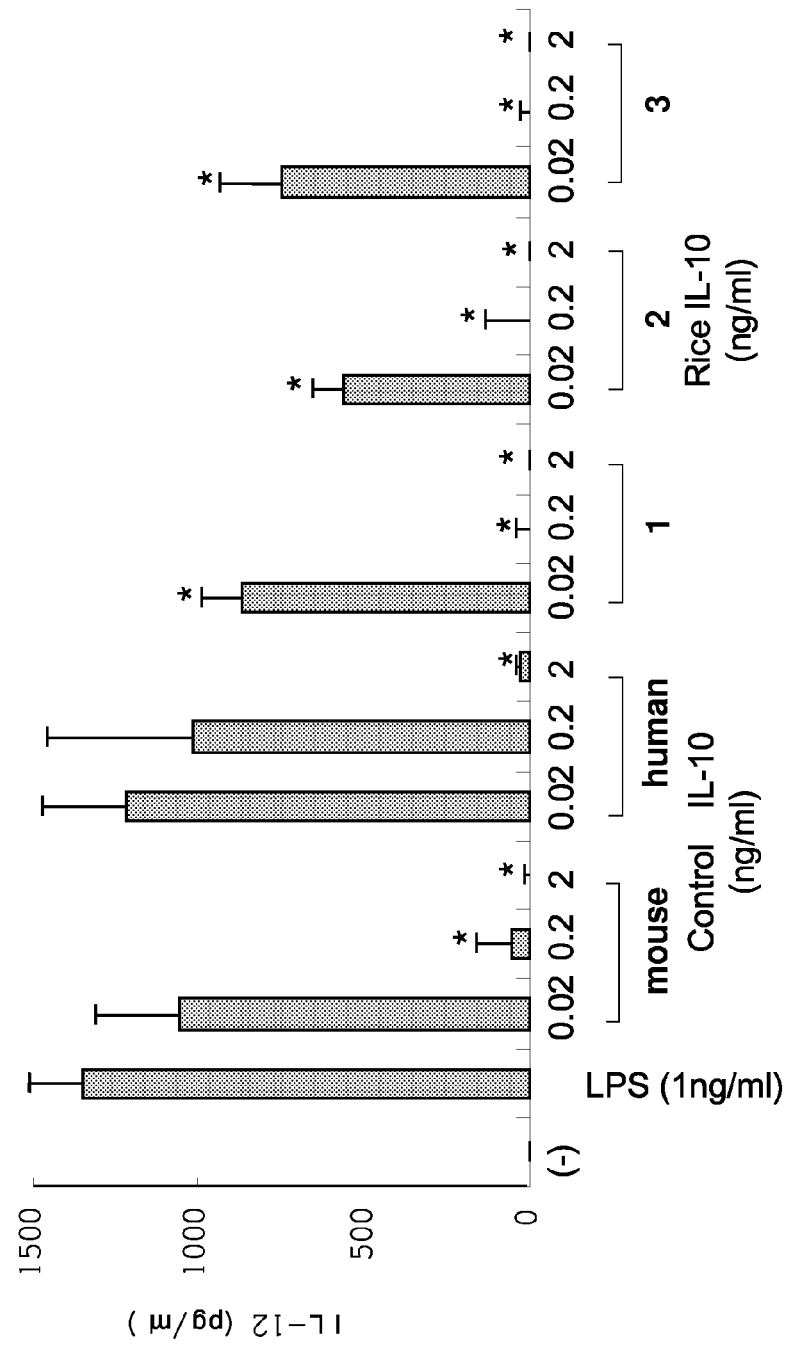
FIG. 9: IL-10 activity levels of purified recombinant hIL-10 by a bioassay method. IL-10 activity was measured by using dendritic cells that were differentiated from cultured mouse bone marrow cells. IL-10 activity levels were determined by the degree of inhibition of IL-12p70 production stimulated by lipopolysaccharide (LPS). Results in FIG. 9 are expressed as mean±standard deviation by analyzing the data from three experiments. Asterisks represent statistical significance compared to LPS induction control (*$P<0.05$).

Bone marrow-derived dendritic cells were used for the IL-10 bioassay (Haase, et al., Immunology 107, 489-499 (2002). Cells were removed from the bone marrow of BALB/c mice and cultured in the presence of granulocyte-macrophage colony-stimulating factor for 8 days. Differentiated dendritic cells were used for the IL-10 bioassay. Interleukin-12p70 was produced by LPS stimulation of the dendritic cells, and IL-12p70 production was inhibited by recombinant IL-10 of the present invention in a dose-dependent manner. The purified recombinant IL-10 was assayed by comparing with standard commercial human and mouse IL-10. Standard IL-10 was purchased from R&D Systems Inc. (Minneapolis, Minn.). The IL-10 activity was measured as the quantitative inhibition of LPS-induced IL-12 production. Human IL-10 standards (2 ng/mL) and mouse IL-10 standards (0.2 ng/mL) almost fully suppressed IL-12 production, and the independently purified recombinant hIL-10 induced full suppression at 0.2 ng/mL and some suppression at even 0.02 ng/mL (FIG. 9). The purified recombinant hIL-10 had at least 10 times higher activity than did commercially available hIL-10.

Endotoxin was measured by the *Limulus amebocyte* lysate method using an Endospecy ES-24S kit with an EG reader SV-12 (Seikagaku Biobusiness Co., Tokyo, Japan) according to the manufacturer's instructions. Endotoxin concentrations in the independently purified recombinant hIL-10 were measured and 0.000024±0000014 EU/μg of endotoxin was detected. Thus, it was confirmed that the purified recombinant hIL-10 contain much lower endotoxin levels compared to recombinant hIL-10 produced by a general method using bacteria (0.1-1 EU/μg).

EXAMPLE 4

Extraction of Recombinant hIL-10 and Removal of Contaminated Seed Proteins Using Extraction Solution Containing Organic Solvent Pulverized rice seeds containing recombinant hIL-10 were obtained according to the method described in EXAMPLE 2, and provided to the following extraction process. Starch granule was removed from the pulverized rice seeds by the DEX/PEG 2-layer distribution method (Ogawa, et al., Plant Cell Physiol. 28, 1517-1527 (1987)), and the resulting purified protein granule was occasionally used in the following extraction process. The extraction of seed proteins and recombinant hIL-10 from the pulverized rice seeds and purified protein granule thereof was performed by a commonly-known method (Ogawa, et al., Plant Cell Physiol. 28, 1517-1527 (1987)).

Each 0.1 g of pulverized rice seeds and purified protein granule thereof was added separately to a 1.5 mL of tube, and a 500 μL of extraction solution was added thereto. Sonication using a homogenizer (TAITEC, VP-5S) was performed (power: 6, 30 seconds) and followed by centrifugation (15,000 G, 10 minutes). The resulting supernatant was separated from the precipitate. A 500 μL of the same extraction solution was added to the precipitate and the same procedure was repeated again in the same manner as above. The resulting supernatants were collected and acetone was added thereto in order to precipitate most of proteins therein. The resulting precipitate was dissolved in the SDS-PAGE sample buffer solution for the electrophoresis thereof. The proteins were separated by the SDS-PAGE method, and the recombinant hIL-10 was specifically detected by staining with Coomassie brilliant blue (CBB), or by the Western blotting method using anti-6His tag antibodies.

Figure 10:
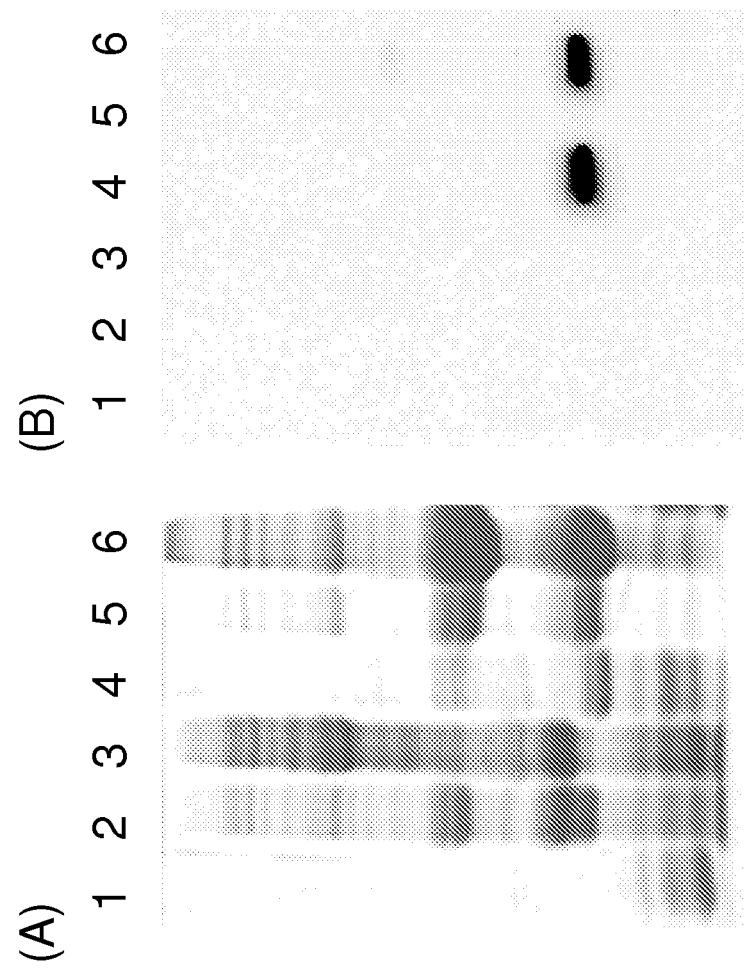
FIG. 10: IL-10 extraction using an extraction solution containing n-propanol and bME. Lane 1: extracted with an extraction solution containing 60 vol % n-propanol and 5 vol % bME. Lane 2: extracted with 1 vol % lactic acid. Lane 3: extracted with 0.5 M NaCl. Lane 4: extracted with an extraction solution containing 60 vol % n-propanol and 5 vol % bME after pre-extraction with 0.5 M NaCl. Lane 5: extracted with 1 vol % lactic acid after pre-extraction with 0.5 M NaCl. Lane 6: extracted with an extraction solution containing 1 wt % cetyl trimethyl ammonium bromide (CTAB), 5 vol % bME, 0.5 M NaCl and 50 mM Tris-HCl (pH 7.4) after pre-extraction with 0.5 M NaCl. Extracted samples were separated by SDS-PAGE, and stained with Coomassie brilliant blue (A) or detected by the Western blotting method using anti-His tag antibodies (B).

As a result, recombinant hIL-10 was not extracted from the pulverized rice seeds and purified protein granule thereof by the commonly-known seed protein extraction method (Ogawa, et al., Plant Cell Physiol. 28, 1517-1527 (1987)) using an extraction solution containing: 60 vol % n-propanol for extracting prolamine; 60 vol % n-propanol and 5 vol % bME for extracting Cys prolamine; 0.5 M NaCl for extracting globulin; and 1 vol % lactic acid after extraction using an extraction solution containing 0.5 M NaCl for extracting glutelin. However, recombinant hIL-10 was extracted by the combination extraction method: pre-extraction using an extraction solution containing 0.5 M NaCl and extraction using an extraction solution containing 60 vol % n-propanol and 5 vol % bME (FIG. 10). Recombinant hIL-10 was extracted when an extraction solution containing 60 vol % n-propanol and 5 vol % bME was used after pre-extraction using an extraction solution containing 0.5 M NaCl, but recombinant hIL-10 was not extracted when an extraction solution containing 60 vol % n-propanol and 5 vol % bME was used alone (FIG. 10, Lanes 1 and 4).

Figure 11:
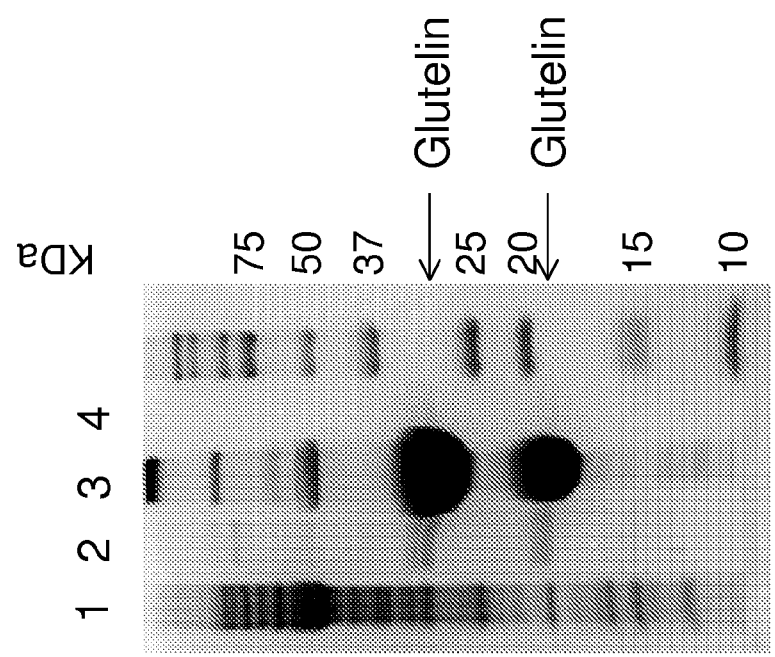
FIG. 11: the results of glutelin extraction from the seeds of transgenic rice plant. Lane 1: extracted with 0.5 M NaCl. Lane 2: extracted with 0.5 M NaCl and then the resulting precipitate was extracted with 1 vol % lactic acid. Lane 3: extracted with 0.5 M NaCl and then the resulting precipitate was extracted with an extraction solution containing 20 vol % acetone, 0.5 M NaCl and 5 vol % bME. Lane 4: Molecular weight markers. Extracted samples were separated by SDS-PAGE, and stained with Coomassie brilliant blue.

Furthermore, the conditions of pre-extraction for removing contaminated seed proteins other than recombinant hIL-10 were studied in order to improve the purity of recombinant hIL-10 by the extraction using an extraction solution containing 60 vol % n-propanol and 5 vol % bME. As a result, it was found that glutelin was much more efficiently extracted by the novel combination method of extraction: the first extraction using an extraction solution containing 0.5 M NaCl and the following second extraction using an extraction solution containing 20 vol % acetone, 0.5 M NaCl and 5 vol % bME than by a commonly-known combination method of extraction (Ogawa, et al., Plant Cell Physiol. 28, 1517-1527 (1987)): the first extraction using an extraction solution containing 0.5 M NaCl and the following second extraction using an extraction solution containing 1 vol % lactic acid (FIG. 11). As glutelin accounts for around 80% of the total seed proteins in a rice seed, the novel combination method of extraction was recognized and used as an outstanding pre-extraction method in order to remarkably improve the purity of extracted recombinant hIL-10.

EXAMPLE 5

Extraction and Removal of Contaminated Seed Proteins Using Extraction Solution Containing Guanidine and Urea Pulverized rice seeds containing recombinant hIL-10 were obtained according to the method described in EXAMPLE 2, and provided to the following extraction process. Extraction solution containing urea or guanidine was prepared and urea was used together with a surfactant.

A 0.1 g of, pulverized rice seeds was added to a 1.5 mL of tube, and a 500 μL of extraction solution containing urea with surfactants or guanidine was added thereto. Sonication using a homogenizer (TAITEC, VP-5S) was performed (power: 6, 30 seconds) and followed by centrifugation (15,000 G, 10 minutes). The resulting supernatant was separated from the precipitate. A 500 μL of the same extraction solution was added to the precipitate and the same procedure was repeated again in the same manner as above.

The resulting supernatants were collected and acetone was added thereto in order to precipitate most of proteins therein. The resulting precipitate was dissolved in the SDS-PAGE sample buffer solution for the electrophoresis thereof. The proteins were separated by the SDS-PAGE method, and the recombinant hIL-10 was specifically detected by staining with Coomassie brilliant blue (CBB), or the Western blotting method using anti 6His tag antibodies.

Figure 12:
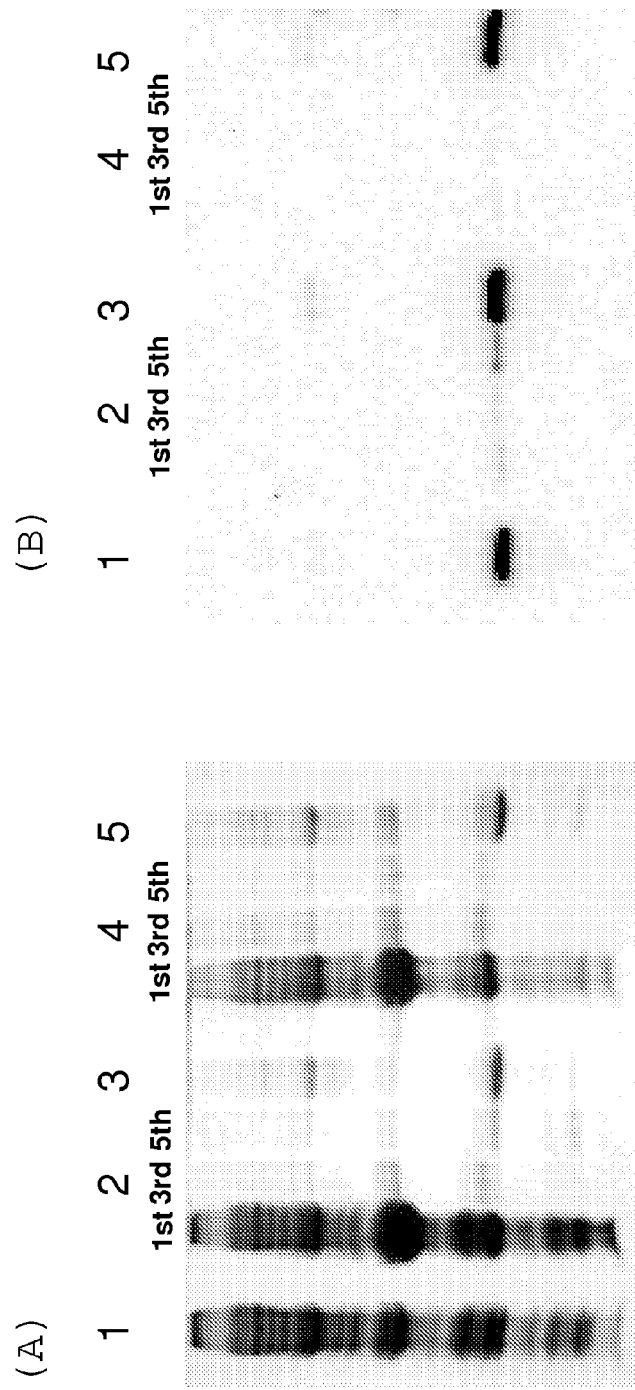
FIG. 12: the efficacy of pre-extraction using an extraction solution containing urea or guanidine. Lane 1: extracted with an extraction buffer solution containing 1 wt % CTAB, 5 vol % bME, 0.5 M NaCl and 50 mM Tris-HCl (pH7.4). Lane 2: pre-extracted with an extraction solution containing 4 M urea and 1 wt % SDS (1st, 3rd and 5th: the results after repeated pre-extractions with this extraction solution). Lane 3: extracted with an extraction buffer solution containing 1 wt % CTAB, 5 vol % bME, 0.5 M NaCl and 50 mM Tris-HCl (pH 7.4) after repeated (five times) pre-extractions with an extraction solution containing 4 M urea and 1 wt % SDS. Lane 4: pre-extracted with 4 M guanidine ($1^{st}$, $3^{rd}$, and $5^{th}$: the results after repeated pre-extractions with this extraction solution). Lane 5: extracted with an extraction buffer solution containing 1 wt % CTAB, 5 vol % bME, 0.5 M NaCl and 50 mM Tris-HCl (pH 7.4) after repeated (five times) pre-extractions with 4 M guanidine. Extracted samples were separated by SDS-PAGE, and stained with Coomassie brilliant blue (A) or detected by the Western blotting method using anti-His tag antibodies (B).

The conditions of pre-extraction for removing contaminated seed proteins other than recombinant hIL-10 were studied in order to improve the purity of recombinant hIL-10 by the extraction using an extraction solution containing reducing agents and surfactants. As a result, it was found that contaminated seed proteins were efficiently extracted by an extraction solution containing 4 M urea and 1 wt % SDS and by an extraction solution containing 4 M guanidine, and by the repeated extraction (FIG. 12). Both extractions were effectively used as the pre-extractions prior to the extraction of recombinant hIL-10 by the extraction solution containing reducing agents and surfactants (1 wt % CTAB, 0.5 M NaCl, 10 mM bME, 50 mM Tris-HCl (pH 7.4)) described in EXAMPLE 2 (FIG. 12).

EXAMPLE 6

Extraction of Recombinant hIL-10 Using Extraction Solution Containing Reducing Agents and Surfactants Pulverized rice seeds containing recombinant hIL-10 were obtained according to the method described in EXAMPLE 2, and provided to the following extraction process.

Extraction and removal of contaminated seed proteins other than recombinant hIL-10 were performed by using the following extraction solutions as described in EXAMPLE 4.

Figure 13:
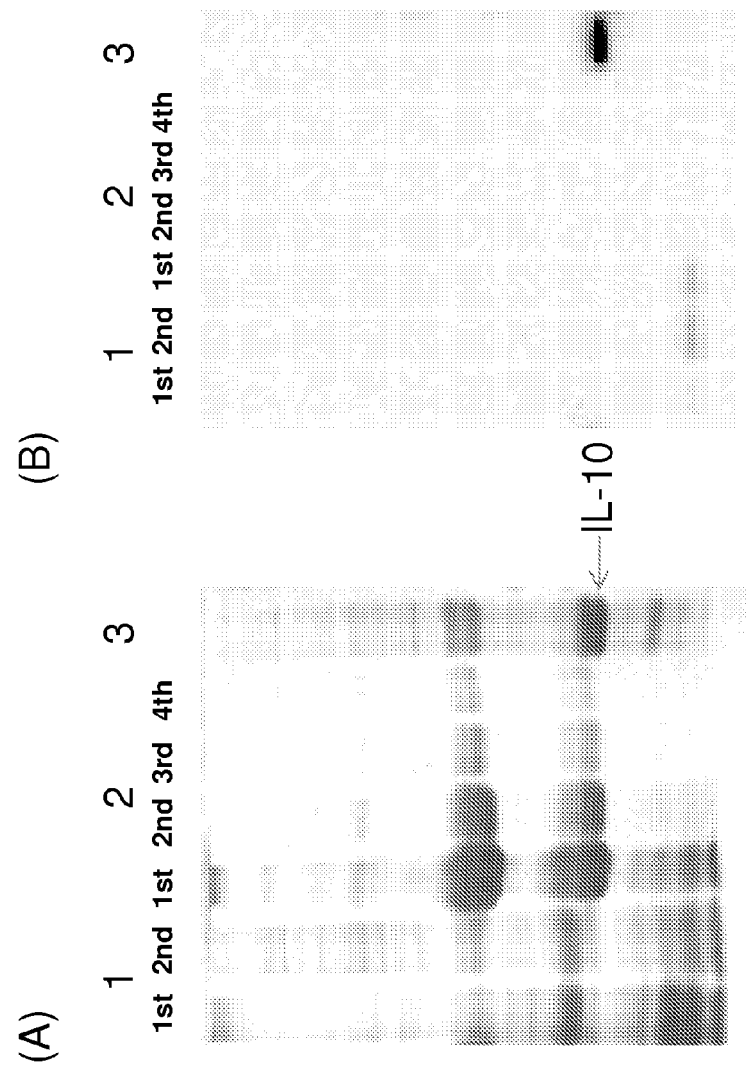
FIG. 13: the efficacy of a series of pre-extractions. Lane l: pre-extracted with an extraction solution containing 60 vol % n-propanol and 0.5M NaCl (1st and 2nd: the results after repeated pre-extractions with this extraction solution). Lane 2: pre-extracted with an extraction solution containing 20 vol % acetone, 0.5 M NaCl and 5 wt % bME ($1^{st}$, $2^{nd}$, $3^{rd}$ and a $4^{th}$: the results after repeated pre-extractions with this extraction solution) after repeated (two times) pre-extractions with an extraction solution containing 60 vol % npropanol and 5 vol % bME. Lane 3: extracted with an extraction buffer solution containing 1 wt % CTAB, 5 vol % bME, 0.5 M NaCl and 50 mM Tris-HCl (pH 7.4) after a series of pre-extractions: first repeated (two times) pre-extractions with an extraction solution containing 60 vol % n-propanol and 5 vol % bME and second repeated (four times) pre-extractions with an extraction solution containing 20 vol % acetone, 0.5 M NaCl and 5 vol % bME. Extracted samples were separated by SDS-PAGE, and stained with Coomassie brilliant blue (A) or detected by the Western blotting method using anti-His tag antibodies (B).

Globulin and prolamine: Extraction solution containing 60 vol % n-propanol and 0.5 M NaCl Glutelin: Extraction solution containing 20 vol % acetone, 0.5 M NaCl, and 5 vol % bME A 0.1 g of pulverized rice seeds was added to a 1.5 mL of tube, and a 500 μL of extraction solution containing 60 vol % n-propanol and 0.5 M NaCl was added thereto. Sonication using a homogenizer (TAITEC, VP-5S) was performed (power: 6, 30 seconds) and followed by centrifugation (15, 000 G, 10 minutes). The resulting supernatant was separated from the precipitate. A 500 μL of the extraction solution containing 20 vol % acetone, 0.5 M NaCl and 5 vol % bME was added to the precipitate and the same procedure was repeated again in the same manner as above. The resulting supernatants were collected and acetone was added thereto in order to precipitate most of proteins therein. The resulting precipitate was dissolved in the SDS-PAGE sample buffer solution for the electrophoresis thereof. The proteins were separated by the SDS-PAGE method, and the recombinant hIL-10 was specifically detected by staining with Coomassie brilliant blue (CBB), or the Western blotting method using anti-His tag antibodies (FIG. 13).

After extracting and removing the contaminated seed proteins by the combination of pre-extractions: the first pre-extraction (repeated twice) of prolamine and globulin using an extraction solution containing 60 vol % n-propanol and 0.5 M NaCl and the following second pre-extraction (repeated four times) of glutelin using an extraction solution containing 20 vol % acetone, 0.5 M NaCl and 5 vol % bME, highly purified recombinant hIL-10 was efficiently extracted by using the extraction solution containing reducing agents and surfactants (1 wt % CTAB, 0.5 M NaCl, 10 mM bME, 50 mM: Tris-HCl pH (7.4)) described in EXAMPLE 2 (FIG. 13).

EXAMPLE 7

Extraction of Recombinant hIL-10 Using Extraction Solution Containing n-Propanol, NaCl and bME Pulverized rice seeds containing recombinant hIL-10 were obtained according to the method described in EXAMPLE 2, and starch granule was removed from the pulverized rice seeds by the DEX/PEG 2-layer distribution method (Ogawa, et al., Plant Cell Physiol 28, 1517-1527 (1987)). The resulting purified protein granule was used in the following extraction process.

Extraction and removal of contaminated seed proteins other than recombinant hIL-10 were performed by using the following extraction solutions as described in EXAMPLE 4.

Figure 14:
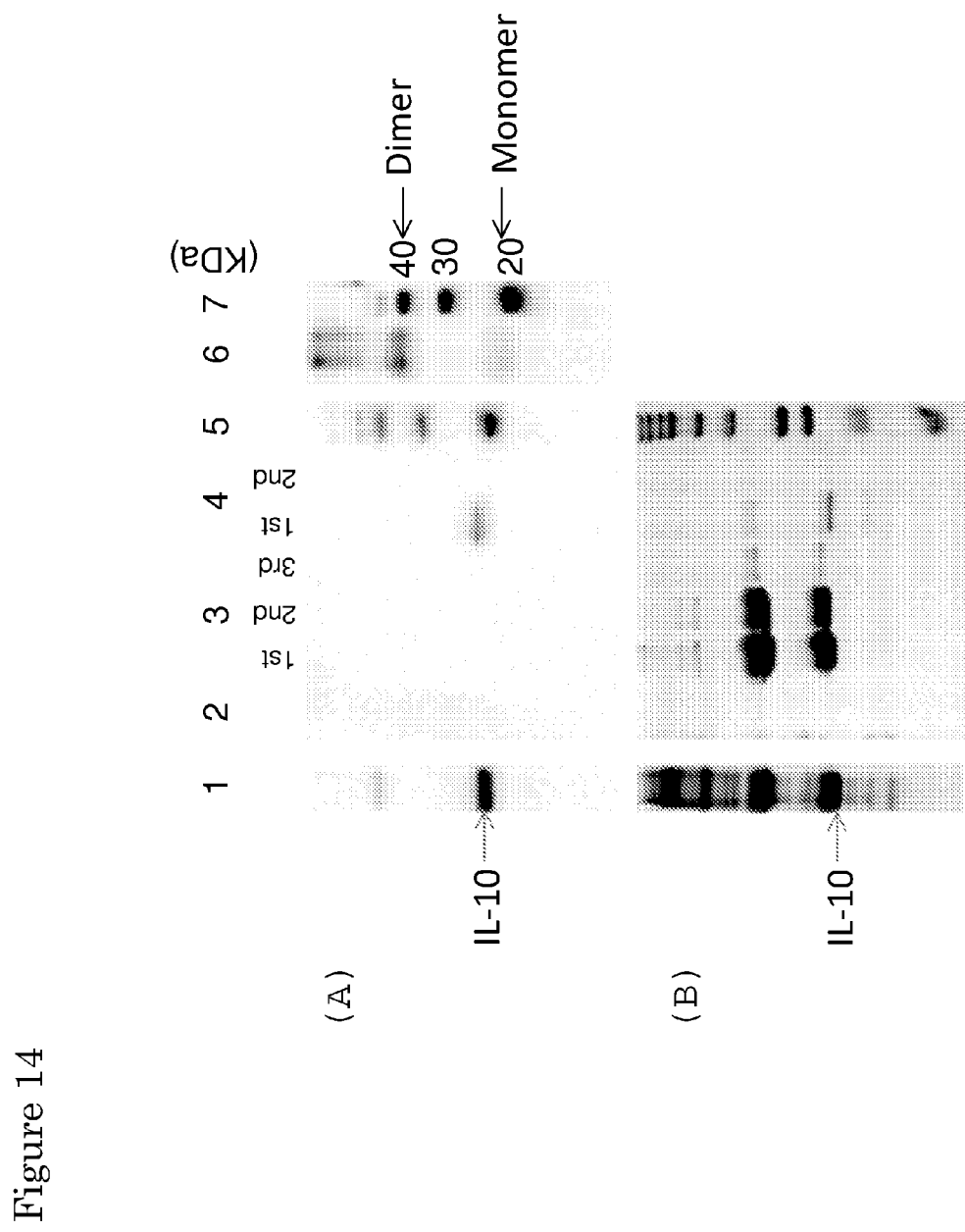
FIG. 14: the efficacy of a series of pre-extractions. Lane 1: extracted with an extraction buffer solution containing 1 wt % CTAB, 5 wt % bME, 0.5 M NaCl and 50 mM Tris-HCl (pH 7.4). Lane 2: pre-extracted with an extraction solution containing 60 vol % n-propanol and 5 vol % bME. Lane 3: pre-extracted with an extraction solution containing 20 vol % acetone, 0.5 M NaCl and 5 wt % bME ($1^{st}$, $2^{nd}$ and $3^{rd}$: the results after repeated pre-extractions with this extraction solution) after pre-extracted with an extraction solution containing 60 vol % n-propanol and 0.5M NaCl. Lane 4: extracted with an extraction solution containing 60 vol % n-propanol and 5 wt % bME ($1^{st}$, and $2^{nd}$: the results after repeated pre-extractions with this extraction solution) after a series of pre-extractions: first pre-extraction with an extraction solution containing 60 vol % n-propanol and 0.5M NaCl and second repeated (three times) pre-extractions with an extraction solution containing 20 vol % acetone, 0.5 M NaCl and 5 vol % bME. Lane 6: treated the extracted sample of lane 4 with BS3 (cross-linking agent). Lane 7: molecular weight markers. Extracted samples were separated by SDS-PAGE, and stained with Coomassie brilliant blue (A) or detected by the Western blotting method using anti-His tag antibodies (B).

Globulin and prolamine: Extraction solution containing 60 vol % n-propanol and 0.5 M NaCl Glutelin: Extraction solution containing 20 vol % acetone, 0.5 M NaCl and 5 wt % bME A 0.1 g of pulverized rice seeds was added to a 1.5 mL of tube, and a 500 μL of the extraction solution containing 60 vol % n-propanol and 0.5 M NaCl was added thereto. Sonication using a homogenizer (TAITEC, VP-5S) was performed (power: 6, seconds) and followed by centrifugation (15,000 G, 10 minutes). The resulting supernatant was separated from the precipitate. A 500 μL of the extraction solution containing 20 vol % acetone, 0.5 M NaCl and 5 vol % bME was added to the precipitate and the same procedure was repeated again in the same manner as above. The resulting supernatants were collected and acetone was added thereto in order to precipitate most of proteins therein. The resulting precipitate was dissolved in the SDS-PAGE sample buffer solution for the electrophoresis thereof. The proteins were separated by the SDS-PAGE method, and the recombinant hIL-10 was specifically detected by staining with Coomassie brilliant blue (CBB), or the Western blotting method using anti-His tag antibodies (FIG. 14).

After extracting and removing the contaminated seed proteins by the combination of pre-extractions: the first pre-extraction of prolamine and globulin using an extraction solution containing 60 vol % n-propanol and 0.5 M NaCl and the following second pre-extraction (repeated three times) of glutelin using an extraction solution containing 20 vol % acetone, 0.5 M NaCl and 5 vol % bME, highly purified recombinant hIL-10 was efficiently extracted by using the extraction solution containing 60 vol % n-propanol, 0.5 M NaCl and 5 vol % bME. Refolding and cross-linking of the extracted recombinant hIL-10 was performed without further purification to give an active form of non-covalent homodimer (FIG. 14).

EXAMPLE 8

Extraction and Purification of Recombinant IL-10

Milli-Q water (Millipore, Bedford, Mass.) was used for the purification experiment. All glassware was dry-heated at 250°

C. for 90 minutes to decompose any endotoxins therein. Extraction buffer solutions were prepared just before use with dry-heated glassware and fresh Milli-Q water. Husks and bran were removed from rice seeds containing recombinant hIL-10 by using FC2 K (Otake Seisakusho, Oharu, Aichi, Japan) and Magic Mill RSKM5B (Satake, Hiroshima, Japan), respectively. The resulting rice seeds were pulverized by using an electric stone mill (F-50, Samap S.A., Andolsheim, France) and was passed through a 355-μm sieve and used for the following extraction process. Forty grams of resulting pulverized rice seeds was mixed with 800 mL of extraction buffer solution (50 mM Tris-HCl (pH 7.4), 0.5 M NaCl) for pre-extraction of seed proteins other than recombinant hIL-10 and extracted overnight at 4° C. by using a magnetic stirrer at 400 rpm. After centrifugation of the resulting mixture at 14,000 G for 10 minutes, the resulting precipitated pellet was re-suspended with 800 mL of extraction buffer solution (50 mM Tris-HCl (pH 7.4), 0.5 M NaCl, 1 wt % cetyl trimethyl ammonium bromide (CTAB) and 10 mM bME) for extraction of recombinant hIL-10 and extracted for 6 hours at 4° C. by using a magnetic stirrer at 400 rpm. After centrifugation of the resulting mixture at 14,000 G for 10 minutes, the resulting precipitated pellet was extracted and centrifuged again in the same manner as above. The supernatant was stored on ice for several hours, and the precipitated CTAB and fine particles were removed by filtration with a nylon mesh and a glass micro fiber filter (GF/A, GE Healthcare), respectively. Imidazole (pH 7.4) was mixed with the resulting extract and adjusted to 20 mM. The extract was applied to a HisTrap FF 5-mL column on an AKTA Prime Plus System (GE Healthcare). His-tagged hIL-10 was eluted with an elution buffer solution (50 mM Tris-HCl (pH 7.4), 0.5 M NaCl, and 0.4 M imidazole). The eluate was precipitated with equal volume of acetone, and resulting precipitate was dissolved in a buffer solution (6 M guanidine hydrochloride, 20 mM Na phosphate (pH 7.4), 0.5 M NaCl, 20 mM imidazole, and 10 mM bME), and re-applied to a HisTrap HP 1-ml column. Recombinant hIL-10 was eluted with a buffer solution (6 M guanidine hydrochloride, 20 mM Na phosphate (pH 7.4), 0.5 M NaCl, 0.4 M imidazole, and 10 mM bME). The eluate was dialyzed overnight with 10 mM Tris-HCl (pH8.0) by a commonly-known dialyzing method and again precipitated with acetone and centrifuged in the same manner as above. Refolding was performed by the dilution method. Recombinant hIL-10 (20 mg) was dissolved in a 0.5 mL of denaturation buffer solution (6 M guanidine hydrochloride, 50 mM Tris-HCl (pH 8.5), 30 mM dithiothreitol). The resulting mixture was diluted with a refolding buffer solution (50 mL of 50 mM Tris-HCl (pH 8.5), 0.4 M arginine hydrochloride, 1 M ammonium thiocyanate, and 0.5 mM oxidized glutathione) and incubated at 33 to 42° C. overnight. The refolded recombinant hIL-10 was dialyzed against phosphate buffered saline at 5° C. overnight, and then dialyzed against 50 mM Tris-HCl (pH 9.0) by a commonly-known dialyzing method. The resulting refolded recombinant hIL-10 was applied to anion exchange column chromatography (HiTrap Q HP, GE Healthcare) with 50 mM Tris-HCl (pH 9.0) for purification, and a linear gradient from 0 to 0.5 M of NaCl was applied to elute the fractions containing the non-covalent homodimer of recombinant hIL-10. The eluate containing the non-covalent homodimer of recombinant hIL-10 was dialyzed with 50 mM MES (pH 6.5) by a commonly-known dialyzing method, applied to cation exchange column chromatography (HiTrap SP, GE Healthcare) for further purification and eluted with a linear gradient from 0 to 0.5 M NaCl. The eluate containing the non-covalent homodimer of recombinant hIL-10 was applied to gel permeation column chromatography (HiPrep Sephacryl S-I00HR, GE Healthcare) for further purification. Purification by a gel filtration column was performed by the column of HiPrep 16/60 Sephacryl S-I00HR (GE Healthcare) using a 50 mM phosphoric acid buffer solution (pH 7.4) containing 150 mM NaCl. Throughout the purification procedure, recombinant hIL-10 was monitored by Western blotting method with the anti-His tag antibodies. After refolding, a crosslink analysis was performed in the same manner as described in EXAMPLE 3 to distinguish non-covalent homodimers and other forms of recombinant hIL-10, and the fractions containing the very purified non-covalent homodimers of recombinant hIL-10 was collected. It was confirmed by the protein analysis described in EXAMPLE 3 that 2 mg (purity: 98%<) of non-covalent homodimers of recombinant hIL-10 was contained in the collected fractions.

It was further confirmed by the measurement of biological activity and endotoxin level in the same manner as described in EXAMPLE 3 that recombinant hIL-10 in the collected fractions fully suppressed IL-12 at 0.2 ng/mL and the endotoxin concentrations therein was 0.000024±0.000014 EU/μg.

Recombinant IL-10, which are derived from vertebrates, mammals, humans, mice, rats, guinea pigs, hamsters, rabbits, dogs, cats, sheep, pigs, cows and horses, and wherein the concentrations of endotoxin is extremely low level such as 0.00001 to 0.00004 EU/μg or 0.0001 EU/μg or less, can be produced in the same manner as above or modified manner thereof from transgenic plants, transgenic monocotyledon and dicotyledon plants that have long been eaten by humans such as tobacco, cabbage, lettuce, rice, potatoes, cucumbers, eggplants, tomatoes, barley, wheat, maize, rye, sorghum, rapeseed, cotton, mustard, *Arabidopsis thaliana*, sunflower, alfalfa, chickpeas, clover, peas, peanuts, yellow split peas, broad beans, *Medicago polymorpha*, cassava, water lentils, water hyacinth, citrus, peaches and apples, organs, tissues, seeds, callus, cells and shoots of transgenic plants, cereal seeds of transgenic grain plants, seeds of rice, wheat, corn and soybean.

What is claimed is:

1. A method for extracting and purifying a recombinant IL-10 protein from a transgenic plant, comprising a step of extracting the recombinant protein by using an extraction solution containing a reducing agent and a surfactant.

2. The method according to claim 1, wherein the extraction is from a part of the transgenic plant selected from the group consisting of an organ, a tissue, a seed, a callus, a cell and a shoot.

3. The method according to claim 2, wherein the extraction is from a seed of the transgenic plant.

4. The method according to claim 1, wherein the recombinant protein is expressed in the transgenic plant, and is in a state selected from the group consisting of:

(a) an encapsulated state in an inclusion body;

(b) an encapsulated state in a protein body;

(c) a state of an aggregated form;

(d) a state where an intra-molecular disulfide bond is formed incorrectly in the recombinant protein;

(e) a state where an inter-molecular non-covalent bond is formed incorrectly between sub-units in the recombinant protein;

(f) a state bonded to a plant protein in the transgenic plant; and (g) a state that substantially only plant protein other than the recombinant protein is extracted by using an extraction solution selected from the group consisting of an extraction solution containing urea, an extraction solution containing guanidine, an extraction solution containing n-propanol, an extraction solution containing n-propanol and β-mercaptoethanol, an extraction solution containing NaCl, an extraction solution containing NaCl and n-propanol, and an extraction solution containing NaCl, n-propanol and β-mercaptoethanol.

5. The method according to claim 1, wherein the transgenic plant is a plant selected from the group consisting of tobacco, cabbage, lettuce, rice, potato, cucumber, eggplant, tomato, barley, wheat, maize, rye, sorghum, rapeseed, cotton, mustard, *Arabidopsis thaliana*, sunflower, alfalfa, chickpea, clover, pea, peanuts, yellow split pea, broad bean, *Medicago polymorpha*, cassava, water lentil, water hyacinth, citrus, peach and apple.

6. The method according to claim 1, wherein the transgenic plant is a rice plant.

7. The method according to claim 1, including an additional pre-extraction step of extracting a plant protein prior to extracting the recombinant protein.

8. The method according to claim 7, wherein the plant protein is extracted by using an extraction solution selected from the group consisting of an extraction solution containing urea, an extraction solution containing guanidine, an extraction solution containing n-propanol, an extraction solution containing n-propanol and β-mercaptoethanol, and an extraction solution containing NaCl, an extraction solution containing NaCl and n-propanol, and an extraction solution containing NaCl, n-propanol and β- mercaptoethanol.

9. The method according to claim 8, wherein the plant protein is selected from the group consisting of prolamine, cys-prolamine, globulin and glutelin.

10. The method according to claim 9, wherein the glutelin is extracted by the steps selected from the group consisting of
   (a) extracting by using an extraction solution containing NaCl and extracting by using an extraction solution containing acetone, NaCl and β-mercaptoethanol; and
   (b) extracting by using an extraction solution containing NaCl and extracting by using an extraction solution containing lactic acid.

11. The method according to claim 1, wherein the reducing agent is a reducing agent having an ability of reducing a disulfide bond.

12. The method according to claim 1, wherein the reducing agent is selected from the group consisting of dithiothreitol, reduced glutathione, β-mercaptoethanol, tris (2-carboxyethyl) phosphine hydrochloride, cysteine, 2-mercaptoethylamine, ascorbic acid and 3-mercaptopropionic acid.

13. The method according to claim 1, wherein the reducing agent is selected from the group consisting of dithiothreitol and β-mercaptoethanol.

14. The method according to claim 1, wherein the surfactant is selected from the group consisting of 3-[(3-cholamidopropyl)dimethylammonio]-1-propanesulfonate, sodium cholate, sodium deoxycholate, sodium lauryl sarcosine, sodium lauryl benzene sulfonate, Triton X-100, Triton X-114, Tween 20, Tween 40, Tween 60, Tween 80, C7BzO, SB3-10, SB3-14, Amidosulfobetaine-14, cetyl trimethylammonium bromide and sodium dodecyl sulfate.

15. The method according to claim 1, wherein the surfactant is selected from the group consisting of cetyl trimethylammonium bromide and sodium dodecyl sulfate.

16. A method for extracting a recombinant IL-10 protein from a transgenic plant, comprising the steps of:
   (a) extracting a plant protein by using an extraction solution selected from the group consisting of an extraction solution containing urea, an extraction solution containing guanidine, an extraction solution containing n-propanol, an extraction solution containing n-propanol and β-mercaptoethanol, an extraction solution containing NaCl, an extraction solution containing NaCl and n-propanol, and an extraction solution containing NaCl, n-propanol and β-mercaptoethanol; and
   (b) extracting the recombinant protein by using an extraction solution containing a water-soluble lower alkanol and a reducing agent having an ability of reducing a disulfide bond.

17. The method according to claim 16, wherein:
   (a) the recombinant protein is a recombinant protein being expressed in the seeds of the transgenic plant and being in a state selected from the group consisting of an encapsulated state in an inclusion body, an encapsulated state in a protein body, an aggregated state, a state where an intra-molecular disulfide bond is formed incorrectly in the recombinant protein, a state where an inter-molecular non-covalent bond is formed incorrectly between sub-units in the recombinant protein, and a state bonded to a plant protein in the transgenic plant;
   (b) the water-soluble lower alkanol is selected from the group consisting of n-propanol, i-propanol, n-butanol, s-butanol, t-butanol; and
   (c) the reducing agent is selected from the group consisting of dithiothreitol, reduced glutathione, β-mercaptoethanol, tris (2-carboxyethyl) phosphine hydrochloride, cysteine, 2-mercaptoethylamine, ascorbic acid and 3-mercaptopropionic acid.

18. The method according to claim 16, wherein the extraction is from a part of the transgenic plant selected from the group consisting of an organ, a tissue, a seed, a callus, a cell and a shoot.

19. The method according to claim 16, wherein the extraction is from a seed of the transgenic plant.

20. The method according to claim 16, wherein the transgenic plant is a plant selected from the group consisting of tobacco, cabbage, lettuce, rice, potato, cucumber, eggplant, tomato, barley, wheat, maize, rye, sorghum, rapeseed, cotton, mustard, *Arabidopsis thaliana*, sunflower, alfalfa, chickpea, clover, pea, peanuts, yellow split pea, broad bean, *Medicago polymorpha*, cassava, water lentil, water hyacinth, citrus, peach and apple.

21. The method according to claim 16, wherein the transgenic plant is a rice plant.

22. The method according to claim 16, comprising the steps of:
   extracting the plant protein by using an extraction solution containing NaCl and
   extracting the recombinant protein by using an extraction solution containing n-propanol and β-mercaptoethanol.

23. The method according to claim 16, wherein the plant protein is selected from the group consisting of prolamine, cys-prolamine, globulin and glutelin.

24. The method according to claim 23, wherein the glutelin is extracted by the steps selected from the group consisting of:
   (a) extracting by using an extraction solution containing NaCl and extracting by using an extraction solution containing acetone, NaCl and β-mercaptoethanol; and
   (b) extracting by using an extraction solution containing NaCl and extracting by using an extraction solution containing lactic acid.

25. The method according to claim 16, including the additional steps for the extracted recombinant protein comprising:
   (a) purifying the extracted recombinant protein by an affinity column chromatography;
   (b) refolding the purified recombinant protein by using a refolding agent; and
   (c) purifying the refolded recombinant protein by an anion exchange column chromatography.

26. The method according to claim 25, including an additional step of denaturing the purified recombinant protein by using a reducing agent having an ability of reducing a disulfide bond before the refolding step.

27. The method according to claim 25, including an additional step of purifying the refolded recombinant protein by a gel filtration column chromatography after the step of purifying the refolded recombinant protein by the anion exchange column chromatography.

28. The method according to claim 25, including an additional step of cross-linking the recombinant protein.

29. The method according to claim 25, wherein the refolding agent is selected from the group consisting of arginine, arginine amide, arginine ethyl ester, lysine, spermidine, spermine, guanidine, guanidine propionate, glycine, proline, urea, sucrose, glucose, N-acetylglucosamine, SDS, Tween 20, sodium sulfate, ammonium sulfate, ammonium iodide, ammonium thiocyanate, taurine, betaine, glycerol, polyol, β-alanine, trimethyl ammonium N-oxide, disaccharide, trehalose, polyethylene glycol, amino acid alkyl ester, amino acid amide, diamine, polyamine, imidazole and histidine.

30. The method according to claim 25, including a process for detecting a biologically active recombinant protein.

31. The method according to claim 30, wherein the detection of the biologically active recombinant protein is performed by a cross-linking reaction.

32. The method according to claim 1, wherein the recombinant protein is a recombinant IL-10 derived from a vertebrate selected from the group consisting of mammal, human, rat, guinea pig, hamster, rabbit, dog, cat, sheep, pig, cow and horse.

33. The method according to claim 32, wherein the recombinant IL-10 is a recombinant hIL-10 derived from a human.

\* \* \* \* \*